(12) United States Patent
Lee et al.

(10) Patent No.: US 8,147,558 B2
(45) Date of Patent: Apr. 3, 2012

(54) MOBILE BEARING ASSEMBLY HAVING MULTIPLE ARTICULATION INTERFACES

(75) Inventors: Jordan S. Lee, Warsaw, IN (US); Daniel D. Auger, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 69 days.

(21) Appl. No.: 12/049,759

(22) Filed: Mar. 17, 2008

(65) Prior Publication Data
US 2008/0243263 A1    Oct. 2, 2008

Related U.S. Application Data

(60) Provisional application No. 60/909,129, filed on Mar. 30, 2007.

(51) Int. Cl.
*A61F 2/38* (2006.01)

(52) U.S. Cl. .................. 623/20.3; 623/20.33

(58) Field of Classification Search .......... 623/20.24, 623/20.26, 20.28–20.34, 20.14–20.16, 20.21, 623/20.27, 21.18
See application file for complete search history.

(56) References Cited

U.S. PATENT DOCUMENTS

| | | | |
|---|---|---|---|
| 3,506,982 A | 4/1970 | Steffee | |
| 3,605,123 A | 9/1971 | Hahn | |
| 3,855,638 A | 12/1974 | Pilliar | |
| 3,906,550 A | 9/1975 | Rostoker et al. | |
| 3,953,899 A | 5/1976 | Charnley | |
| 4,016,606 A | 4/1977 | Murray et al. | |
| 4,205,400 A | 6/1980 | Shen et al. | |
| 4,207,627 A | 6/1980 | Cloutier | |
| 4,213,816 A | 7/1980 | Morris | |
| 4,216,549 A | 8/1980 | Hillberry et al. | |
| 4,224,696 A | 9/1980 | Murray et al. | |
| 4,224,697 A | 9/1980 | Murray et al. | |
| 4,340,978 A | 7/1982 | Buechel et al. | |
| 4,454,612 A | 6/1984 | McDaniel et al. | |
| 4,470,158 A | 9/1984 | Pappas et al. | |
| 4,479,271 A | 10/1984 | Bolesky | |
| 4,501,031 A | 2/1985 | McDaniel et al. | |
| 4,568,348 A | 2/1986 | Johnson et al. | |
| 4,589,883 A | 5/1986 | Kenna | |
| 4,636,219 A | 1/1987 | Pratt et al. | |
| 4,718,413 A | 1/1988 | Johnson | |

(Continued)

FOREIGN PATENT DOCUMENTS

BE    1008201    2/1996

(Continued)

OTHER PUBLICATIONS

"The Oxford Partial Knee", Biomet Patients and Caregivers-Joint Replacement, www.biomet.com/patients/oxford.cfm, Biomet, Inc. 2008, 3 pages.

(Continued)

*Primary Examiner* — David Isabella
*Assistant Examiner* — Marcia Hoffman
(74) *Attorney, Agent, or Firm* — Barnes & Thornburg LLP

(57) ABSTRACT

A mobile tibial assembly includes a tibial tray, a tibial insert, and a platform separate from the tibial tray and the tibial insert. The platform is configured to be coupled to the tibial insert and the tibial tray. The tibial insert is movable relative to the platform and the platform is movable relative to the tibial tray.

13 Claims, 19 Drawing Sheets

U.S. PATENT DOCUMENTS

| | | | |
|---|---|---|---|
| 4,719,908 A | 1/1988 | Averill et al. | |
| 4,728,332 A | 3/1988 | Albrektsson | |
| 4,743,261 A | 5/1988 | Epinette | |
| 4,795,468 A | 1/1989 | Hodorek et al. | |
| 4,911,721 A | 3/1990 | Albrektsson | |
| 4,936,847 A | 6/1990 | Manginelli | |
| 4,944,757 A | 7/1990 | Martinez et al. | |
| 4,950,298 A | 8/1990 | Gustilo et al. | |
| 4,997,445 A | 3/1991 | Hodorek | |
| 5,019,103 A | 5/1991 | Van Zile et al. | |
| 5,047,058 A | 9/1991 | Roberts et al. | |
| 5,108,452 A | 4/1992 | DeMane et al. | |
| 5,152,797 A | 10/1992 | Luckman et al. | |
| 5,201,769 A | 4/1993 | Schutzer | |
| 5,226,915 A | 7/1993 | Bertin | |
| 5,263,987 A | 11/1993 | Shah | |
| 5,282,868 A | 2/1994 | Bahler | |
| 5,330,532 A | 7/1994 | Ranawat | |
| D354,810 S | 1/1995 | Nazre | |
| 5,395,401 A * | 3/1995 | Bahler | 623/20.29 |
| D357,534 S | 4/1995 | Hayes | |
| D359,557 S | 6/1995 | Hayes | |
| 5,458,637 A | 10/1995 | Hayes | |
| 5,609,639 A | 3/1997 | Walker | |
| 5,609,640 A | 3/1997 | Johnson | |
| 5,658,341 A | 8/1997 | Delfosse | |
| 5,702,458 A | 12/1997 | Burstein et al. | |
| 5,702,459 A | 12/1997 | Hummer et al. | |
| 5,716,361 A | 2/1998 | Masini | |
| 5,755,801 A | 5/1998 | Walker et al. | |
| 5,800,560 A * | 9/1998 | Draenert | 623/22.43 |
| 5,810,827 A | 9/1998 | Haines et al. | |
| 5,824,106 A | 10/1998 | Fournol | |
| 5,855,296 A | 1/1999 | McCann et al. | |
| 5,871,541 A | 2/1999 | Gerber | |
| 5,879,354 A | 3/1999 | Haines et al. | |
| 5,888,034 A | 3/1999 | Greenberg | |
| 5,944,722 A | 8/1999 | Masini | |
| 5,947,973 A | 9/1999 | Masini | |
| 5,957,926 A | 9/1999 | Masini | |
| 5,957,979 A | 9/1999 | Beckman et al. | |
| 5,961,523 A | 10/1999 | Masini | |
| 5,971,989 A | 10/1999 | Masini | |
| 6,004,351 A | 12/1999 | Tomita et al. | |
| 6,010,534 A * | 1/2000 | O'Neil et al. | 623/20.34 |
| 6,019,767 A | 2/2000 | Howell | |
| 6,039,764 A | 3/2000 | Pottenger et al. | |
| 6,056,754 A | 5/2000 | Haines et al. | |
| 6,068,633 A | 5/2000 | Masini | |
| 6,077,269 A | 6/2000 | Masini | |
| 6,102,916 A | 8/2000 | Masini | |
| 6,106,529 A | 8/2000 | Techiera | |
| 6,123,728 A | 9/2000 | Brosnahan et al. | |
| 6,139,581 A | 10/2000 | Engh et al. | |
| 6,171,340 B1 | 1/2001 | McDowell | |
| 6,187,010 B1 | 2/2001 | Masini | |
| 6,197,064 B1 | 3/2001 | Haines et al. | |
| 6,214,011 B1 | 4/2001 | Masini | |
| 6,254,604 B1 | 7/2001 | Howell | |
| 6,254,605 B1 | 7/2001 | Howell | |
| 6,296,666 B1 | 10/2001 | Gardner | |
| 6,361,564 B1 | 3/2002 | Marceaux et al. | |
| 6,419,707 B1 | 7/2002 | Leclercq | |
| 6,428,577 B1 | 8/2002 | Evans et al. | |
| 6,494,914 B2 | 12/2002 | Brown et al. | |
| 6,503,254 B2 | 1/2003 | Masini | |
| 6,506,215 B1 | 1/2003 | Letot et al. | |
| 6,520,964 B2 | 2/2003 | Tallarida et al. | |
| 6,602,292 B2 | 8/2003 | Burkinshaw | |
| 6,616,696 B1 | 9/2003 | Merchant | |
| 6,660,039 B1 | 12/2003 | Evans et al. | |
| 6,702,821 B2 | 3/2004 | Bonutti | |
| 6,730,128 B2 | 5/2004 | Burstein | |
| 6,770,078 B2 | 8/2004 | Bonutti | |
| 6,869,448 B2 | 3/2005 | Tuke et al. | |
| 6,916,341 B2 | 7/2005 | Rolston | |
| 6,946,001 B2 | 9/2005 | Sanford et al. | |
| 7,033,397 B2 | 4/2006 | Webster et al. | |
| 7,101,401 B2 | 9/2006 | Brack | |
| 7,105,027 B2 | 9/2006 | Lipman et al. | |
| 7,115,131 B2 | 10/2006 | Engh et al. | |
| 7,708,741 B1 | 5/2010 | Bonutti | |
| 7,931,690 B1 | 4/2011 | Bonutti | |
| 2001/0037155 A1 | 11/2001 | Merchant | |
| 2002/0055784 A1 * | 5/2002 | Burstein et al. | 623/20.28 |
| 2003/0009232 A1 | 1/2003 | Metzger et al. | |
| 2003/0028196 A1 | 2/2003 | Bonutti | |
| 2003/0033018 A1 | 2/2003 | Merchant | |
| 2003/0120346 A1 | 6/2003 | Mercinek et al. | |
| 2003/0158606 A1 | 8/2003 | Coon et al. | |
| 2003/0181984 A1 | 9/2003 | Abendschein | |
| 2003/0187510 A1 | 10/2003 | Hyde | |
| 2003/0195633 A1 | 10/2003 | Hyde | |
| 2004/0006394 A1 | 1/2004 | Lipman et al. | |
| 2004/0039447 A1 | 2/2004 | Simon et al. | |
| 2004/0107000 A1 | 6/2004 | Felt et al. | |
| 2004/0143338 A1 | 7/2004 | Burkinshaw et al. | |
| 2004/0153066 A1 | 8/2004 | Coon et al. | |
| 2004/0153164 A1 | 8/2004 | Sanford et al. | |
| 2004/0167630 A1 | 8/2004 | Rolston | |
| 2004/0193280 A1 | 9/2004 | Webster et al. | |
| 2004/0254645 A1 | 12/2004 | Arnin et al. | |
| 2005/0015153 A1 | 1/2005 | Goble et al. | |
| 2005/0027365 A1 | 2/2005 | Burstein et al. | |
| 2005/0096747 A1 | 5/2005 | Tuttle et al. | |
| 2005/0119663 A1 | 6/2005 | Keyer et al. | |
| 2005/0119664 A1 | 6/2005 | Carignan et al. | |
| 2005/0143830 A1 | 6/2005 | Marcinek et al. | |
| 2005/0143831 A1 | 6/2005 | Justin et al. | |
| 2005/0143833 A1 | 6/2005 | Merchant | |
| 2005/0149041 A1 | 7/2005 | McGinley et al. | |
| 2005/0171604 A1 | 8/2005 | Michalow | |
| 2005/0171612 A1 | 8/2005 | Rolston | |
| 2005/0177242 A1 | 8/2005 | Lotke | |
| 2005/0197709 A1 | 9/2005 | Schaefer et al. | |
| 2005/0203384 A1 | 9/2005 | Sati et al. | |
| 2005/0234465 A1 | 10/2005 | McCombs et al. | |
| 2005/0240273 A1 * | 10/2005 | Khandkar et al. | 623/17.15 |
| 2005/0278034 A1 | 12/2005 | Johnson et al. | |
| 2006/0004460 A1 | 1/2006 | Engh et al. | |
| 2006/0009776 A1 | 1/2006 | Justin et al. | |
| 2006/0009854 A1 | 1/2006 | Justin et al. | |
| 2006/0009855 A1 | 1/2006 | Goble et al. | |
| 2006/0030855 A1 | 2/2006 | Haines | |
| 2006/0030945 A1 | 2/2006 | Wright | |
| 2006/0085072 A1 | 4/2006 | Funk et al. | |
| 2006/0089720 A1 | 4/2006 | Schneier | |
| 2006/0122616 A1 | 6/2006 | Bennett et al. | |
| 2006/0129246 A1 | 6/2006 | Steffensmeier | |
| 2006/0190086 A1 | 8/2006 | Clemow et al. | |
| 2006/0195195 A1 | 8/2006 | Burstein et al. | |
| 2006/0195196 A1 | 8/2006 | Pendleton et al. | |
| 2006/0235537 A1 | 10/2006 | Kuczynski et al. | |
| 2006/0265079 A1 | 11/2006 | D'Alessio | |
| 2007/0010890 A1 | 1/2007 | Collazo | |
| 2007/0100459 A1 | 5/2007 | Rhodes | |
| 2007/0100460 A1 | 5/2007 | Rhodes | |
| 2008/0033567 A1 | 2/2008 | Stchur | |
| 2008/0086210 A1 | 4/2008 | Fox | |

FOREIGN PATENT DOCUMENTS

| | | |
|---|---|---|
| DE | 10012060 | 9/2001 |
| DE | 10053623 A1 | 5/2002 |
| EP | 0135319 A2 | 3/1985 |
| EP | 0183670 | 6/1986 |
| EP | 0327387 A2 | 8/1989 |
| EP | 0328463 A1 | 8/1989 |
| EP | 0874596 A1 | 11/1998 |
| EP | 0709075 B1 | 8/2001 |
| EP | 1327424 | 7/2003 |
| EP | 1329205 A1 | 7/2003 |
| EP | 1374782 A2 | 1/2004 |
| EP | 1442726 | 8/2004 |
| EP | 1442728 A2 | 8/2004 |
| EP | 1550418 | 7/2005 |
| EP | 1557144 A1 | 7/2005 |
| EP | 1584309 | 10/2005 |

| | | | |
|---|---|---|---|
| EP | 1669034 A1 | 6/2006 |
| EP | 1702590 A2 | 9/2006 |
| EP | 1741412 | 1/2007 |
| FR | 2663536 | 12/1991 |
| FR | 2702369 | 9/1994 |
| FR | 2721820 | 1/1996 |
| FR | 2885516 A1 | 11/2006 |
| GB | 2355935 | 5/2001 |
| JP | 2002272756 A | 9/2002 |
| WO | 9110412 A1 | 7/1991 |
| WO | 9524874 A1 | 9/1995 |
| WO | 9716129 A1 | 5/1997 |
| WO | 0013616 A1 | 3/2000 |
| WO | 0170143 A1 | 9/2001 |
| WO | 0209623 A1 | 2/2002 |
| WO | 03068119 A2 | 8/2003 |
| WO | 2004001569 A2 | 12/2003 |
| WO | 2005009298 A1 | 2/2005 |
| WO | 2005025451 A2 | 3/2005 |
| WO | 2005037065 A2 | 4/2005 |
| WO | 2005044150 A1 | 5/2005 |
| WO | 2005069957 A2 | 8/2005 |
| WO | 2006074503 A1 | 7/2006 |
| WO | 2006078511 A1 | 7/2006 |
| WO | 2006078528 A2 | 7/2006 |
| WO | 2006078864 A1 | 7/2006 |
| WO | 2006106419 A2 | 10/2006 |
| WO | 2006112911 A2 | 10/2006 |

OTHER PUBLICATIONS

"Preservation Uni-compartmental Knee", DePuy Orthopaedics, Inc. 2002, 31 pages.

European Search Report for European Patent Application No. 08251209.6-2310, Jul. 9, 2008, 7 pgs.

Extended European Search Report for European Patent Application No. 10189885.6-2310, Mar. 18, 2011, 7 pages.

European Search Report for European Patent Application No. 08251213.8-2310, Jul. 9, 2008, 7 pgs.

European Search Report for European Patent Application No. 08251211.2-2310, Jul. 21, 2008, 7 pgs.

European Search Report for European Patent Application No. 08251212.0-2310, Jul. 21, 2008, 7 pgs.

Extended European Search Report for European Patent Application No. 08251210.4-2310, Jun. 20, 2008, 7 pgs.

Extended European Search Report for European Patent Application No. 10189881.5-2310, Feb. 17, 2011, 6 pgs.

Chinese First Office Action, Chinese Patent Application No. 200810128765.8, Aug. 15, 2011, 8 pages.

Chinese First Office Action, Chinese Patent Application No. 200810125845.8, Aug. 24, 2011, 7 pages.

* cited by examiner

MOBILE BEARING ASSEMBLY HAVING MULTIPLE ARTICULATION INTERFACES

This patent application claims priority to and the benefit of U.S. Provisional Patent Application Ser. No. 60/909,129 entitled "Mobile Bearing Assembly Having Multiple Articulation Interfaces" by Jordan S. Lee et al., which was filed on Mar. 30, 2007, the entirety of which is expressly incorporated herein by reference.

CROSS REFERENCE TO RELATED APPLICATIONS

Cross-reference is made to U.S. Utility patent application Ser. No. 12/049,753 entitled "MOBILE BEARING ASSEMBLY," which was filed on Mar. 17, 2008 by Jordan S. Lee et al. (265280-204350), to U.S. Utility patent application Ser. No. 11/694,389 entitled "MOBILE BEARING ASSEMBLY HAVING OFFSET DWELL POINT," which was filed on Mar. 30, 2007 by Jordan S. Lee et al. (265280-201238), to U.S. Utility patent application Ser. No. 12/049,750 entitled "MOBILE BEARING ASSEMBLY HAVING A CLOSED TRACK," which was filed on Mar. 17, 2008 by Joseph G. Wyss et al. (265280-204351), and to U.S. Utility patent application Ser. No. 12/049,699 entitled "MOBILE BEARING ASSEMBLY HAVING A NON-PLANAR INTERFACE SURFACE," which was filed on Mar. 17, 2008 by Jordan S. Lee et al. (265280-204348), the entirely of all of which is expressly incorporated herein by reference.

TECHNICAL FIELD

The present disclosure relates generally to orthopaedic prostheses, and particularly to tibial assemblies including a tibial tray and a tibial insert.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements in which a unicompartmental tibial insert is used to replace each of the medial and lateral condyles of the patient. A single, total femoral component or two partial femoral components may be used to cooperate with the two unicompartmental inserts.

In addition, in some knee replacement procedures, a total knee tibial tray may used with a unicompartmental tibial insert. For example, a total knee tibial tray may be used with a single unicompartmental tibial insert to replace either the medial or lateral condyle of the patient's knee. Alternatively, a total knee tibial tray may be used with two unicompartmental tibial inserts, each replacing one of the medial and lateral condyles of the patient's knee. In such applications, the medial and lateral unicompartmental tibial inserts may have different characteristics and be selected based on the orthopaedic considerations associated with the respective condyle of the patient's knee.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery.

A tibial assembly of a unicompartmental knee prosthesis typically includes a tibial tray configured to be coupled to the patient's tibia and a polymer tibial bearing or insert adjacent the tibial tray. As discussed above, the tibial tray may be a total or unicompartmental tibial tray. The tibial insert includes an upper bearing surface configured to engage a corresponding articulating condylar surface of a femoral component coupled to the patient's femur. A mobile tibial assembly generally refers to a tibial assembly wherein the tibial insert is movable relative to the tibial tray. In other words, the tibial insert may rotate relative to the tray and/or the tibial insert may move medially, laterally, anteriorly, and/or posteriorly relative to the tibial tray. This motion of the tibial insert relative to the tray may be constrained in any number of ways in order to limit the type of motion of the tibial insert. For example, the tibial insert may be limited to anterior/posterior motion relative to the tibial tray and/or rotation of the tibial insert relative to the tibial tray may be limited to something less than 360 degree rotation. A fixed tibial assembly generally refers to a tibial assembly wherein the tibial insert is not movable relative to the tibial tray and remains in a fixed location thereon. Surgeons may choose between fixed and mobile tibial assemblies depending upon the particular needs of the patient.

Typical mobile tibial assemblies fall into one of two classifications with respect to the insert-to-tray interface: unconstrained and constrained. In an unconstrained mobile tibial assembly, the tibial insert is free to move in all directions relative to the tibial tray. In a constrained mobile tibial assembly, the tibial insert is typically restricted from movement relative to the tibial tray in all but one or more directions and/or movements (e.g., translations and/or rotations).

SUMMARY

According to one aspect, a unicompartmental mobile tibial assembly may include a tibial tray, a tibial insert, and a platform separate from the tibial tray and the tibial insert. The tibial tray may be configured to be coupled to a surgically-prepared surface of the proximal end of a tibia. The tibial insert may include an upper bearing surface configured to contact a surgically-prepared surface of the distal end of a femur. The platform may be configured to be coupled to the tibial tray and the tibial insert, wherein the platform is movable relative to the tibial tray and the tibial insert is movable relative to the platform.

In some embodiments, the tibial tray may include an upper surface having a convex bearing defined thereon. In such embodiments, the platform may include a bottom surface having a concave recess defined therein. The concave recess of the bottom surface of the platform may be configured to receive a portion of the convex bearing of the tibial tray. As such, the platform may be configured to move along the convex bearing of the tibial tray. For example, the platform may be configured to move along the convex bearing in a medially-laterally direction relative to the tibial tray.

Additionally or alternatively, the platform may include a top surface having a concave recess defined therein in some embodiments. The concave recess of the top surface of the platform may be configured to receive a portion of the tibial insert. In such embodiments, the tibial insert may include a convex bottom surface configured to be received by the concave recess defined in the top surface of the platform. As such, the tibial insert may be configured to move within the concave recess in a generally anterior-posterior direction.

In some embodiments, the platform may include a first elongated concave recess and a second elongated convex recess. The first elongated concave recess may be defined in a top surface of the platform. The second elongated concave recess may be defined in a bottom surface of the platform. The first elongated concave recess may be longitudinally aligned in a generally anterior-posterior direction. The second elongated concave recess maybe longitudinally aligned in a medially-laterally direction.

In other embodiments, the tibial tray may include an upper surface and a track defined therein. In such embodiments, a portion of the platform may be configured to be inserted into the track such that the platform is movable relative to the tibial tray along the track. The track may be embodied or otherwise include a bottom wall, a first side wall, a second side wall, a first lip extending from the first side wall over a portion of the bottom wall, and a second lip extending from the second wall over a portion of the bottom wall. The first and second lips may define an opening therebetween. The track may be positioned in the upper surface of the tibial tray such that the platform moves in a generally anterior-posterior direction with respect to the tibial tray when moved along the track.

In some embodiments, the platform may include a top surface and a stem extending upwardly therefrom. In such embodiments, the stem may extend past the upper surface of the tibial tray when the portion of the platform is inserted into the tibial tray. Additionally, in such embodiments, the tibial insert may include a bottom surface having a track defined therein. The track of the tibial insert may be configured to receive the stem of the tibial tray. The track of the tibial insert may be embodied as or otherwise include a bottom wall, a first side wall, a second side wall, a first lip extending from the first side wall over a portion of the bottom wall, and a second lip extending from the second wall over a portion of the bottom wall. The first and second lips of the track of the tibial insert defining an opening therebetween.

In some embodiments, each of the first and second lips of the track of the tibial insert may include a bottom wall oblique to the bottom wall of the track of the tibial insert. In such embodiments, the stem of the tibial insert may include a flange The flange may include a bottom surface and a top surface. The bottom surface may be configured to contact the bottom wall of the track of the tibial insert when the stem is received thereby. The top surface may be oblique to the bottom surface of the flange. Additionally, the top surface may be configured to contact the bottom surface of at least one of the first lip and the second lip of the track of the tibial insert when the stem is received thereby.

In other embodiments, each of the first and second lips may include a bottom wall substantially parallel to the bottom wall of the track. Alternatively, in other embodiments, the bottom wall of the first and second lips may be oblique to the bottom wall of the track. The stem may include a flange. The flange may include a bottom surface and a top surface. The bottom surface of the flange may be configured to contact the bottom wall of the track of the tibial insert when the stem is received thereby. The top surface of the flange may be substantially parallel to the bottom surface of the flange. Additionally, the top surface of the flange may be configured to contact the bottom surface of at least one of the first lip and the second lip of the track of the tibial insert when the stem is received thereby.

As discussed above, the stem may include a flange defined at the end of a neck in some embodiments. The flange may have a rectangular bottom profile, an elliptical bottom profile, a triangular bottom profile, a hexagonal or other polygonal or substantially polygonal bottom profile, or the like when viewed in plan view. In embodiments wherein the flange has a rectangular bottom profile, the flange may be configured to restrict the movement of the tibial insert with respect to the platform to a single direction when stem is received by the track of the tibial insert.

In some embodiments, the tibial insert may include a bottom surface and a stem extending downwardly from the bottom surface. In such embodiments, the platform may include an aperture configured to receive the stem of the tibial insert. The stem may, for example, be a substantially cylindrical stem. The tibial insert may be configured to rotate about an axis defined by the stem when the stem is received by the aperture of the platform.

As discussed above, the tibial insert may be configured to move relative to the platform and the platform may be configured to move relative to the tibial tray. For example, the tibial insert may be configured to move in a generally anterior-posterior direction relative to the platform and the platform may be configured to move in an medially-laterally direction relative to the tibial tray. Additionally or alternatively, the tibial insert may be configured to move in an medially-laterally direction relative to the platform and the platform may be configured to move in a generally anterior-posterior direction relative to the tibial tray. Additionally or alternatively, the tibial insert may be configured to rotate about an axis relative to the platform. Additionally or alternatively, the platform may be configured to move in a generally anterior-posterior direction relative to the tibial tray and the tibial insert may be configured to rotate about an axis relative to the platform. Additionally or alternatively, the tibial insert may be configured to transversely move relative to the platform and rotate about an axis defined by a stem of the platform.

According to another aspect, a unicompartmental mobile tibial assembly may include a tibial tray, a tibial insert, and a platform separate form the tibial tray and the tibial insert. The tibial tray may be configured to be coupled to a surgically-prepared surface of the proximal end of a tibia. Additionally, the tibial tray may include an upper surface and a track defined therein. The tibial insert may include an upper bearing surface configured to be receive a surgically-prepared surface of the distal end of a femur. A portion of the platform may be configured to be inserted into the track of the tibial tray such that the platform is movable relative to the tibial tray. Additionally, the platform may be configured to be coupled to the tibial tray such that the tibial tray is movable relative to the platform.

In some embodiments, the platform may include a top surface and a stem extending upwardly therefrom. In such embodiments, the tibial insert may include a bottom surface having a track defined therein. The track of the tibial insert may be configured to receive the stem of the tibial tray. The track may be defined in the upper surface of the tibial tray in a generally anterior-posterior direction, a generally medial-lateral direction, or some combination thereof (i.e., a generally diagonal direction). Additionally, the track may have a substantially straight top profile or may have a curved stop profile in some embodiments. The stem may include a flange defined at one end. The flange may have a rectangular bottom profile, an elliptical bottom profile, a triangular bottom profile, a hexagonal or other polygonal or substantially polygonal bottom profile, or the like when viewed in plan view.

In some embodiments, the tibial insert may include a bottom surface and a stem extending downwardly from the bottom surface. In such embodiments, the platform may include an aperture configured to receive the stem of the tibial insert. The stem may be embodied as, for example, a substantially cylindrical stem. Additionally, in such embodiments, the tibial insert may be configured to rotate about an axis defined by the stem when the stem is received by the aperture of the platform.

According to a further aspect, a method for implanting a unicompartmental tibial assembly may include securing a tibial tray to a surgically-prepared surface of the proximal end of a tibia, coupling a platform to the tibial tray, and coupling a tibial insert to the platform. The method may also include moving the platform relative to the tibial tray and/or moving the tibial insert relative to the platform. For example, the method may include moving the platform relative to the tibial tray in a first direction and moving the tibial insert relative to the platform in a second direction. The first and second directions may be different directions. Additionally or alternatively, the method may include translating the platform relative to the tibial tray and rotating the tibial insert about an axis. Additionally or alternatively, the method may include translating the platform relative to the tibial tray, translating the tibial insert relative to the platform, and rotating the tibial insert about an axis. Additionally or alternatively, the method may rotating the platform about an axis relative to the tibial tray and translating the tibial insert relative to the platform.

According to yet a further aspect, a method for implanting a tibial assembly may include securing a tibial tray to a surgically-prepared surface of the proximal end of a tibia. The method may also include coupling a platform to the tibial tray such that the platform is movable in a single direction relative to the tibial tray. Additionally, the method may include coupling a tibial insert to the platform such that the tibial insert is movable in a single direction relative to the platform.

BRIEF DESCRIPTION OF THE DRAWINGS

The detailed description particularly refers to the following figures, in which.

DETAILED DESCRIPTION OF THE DRAWINGS

Figure 1:
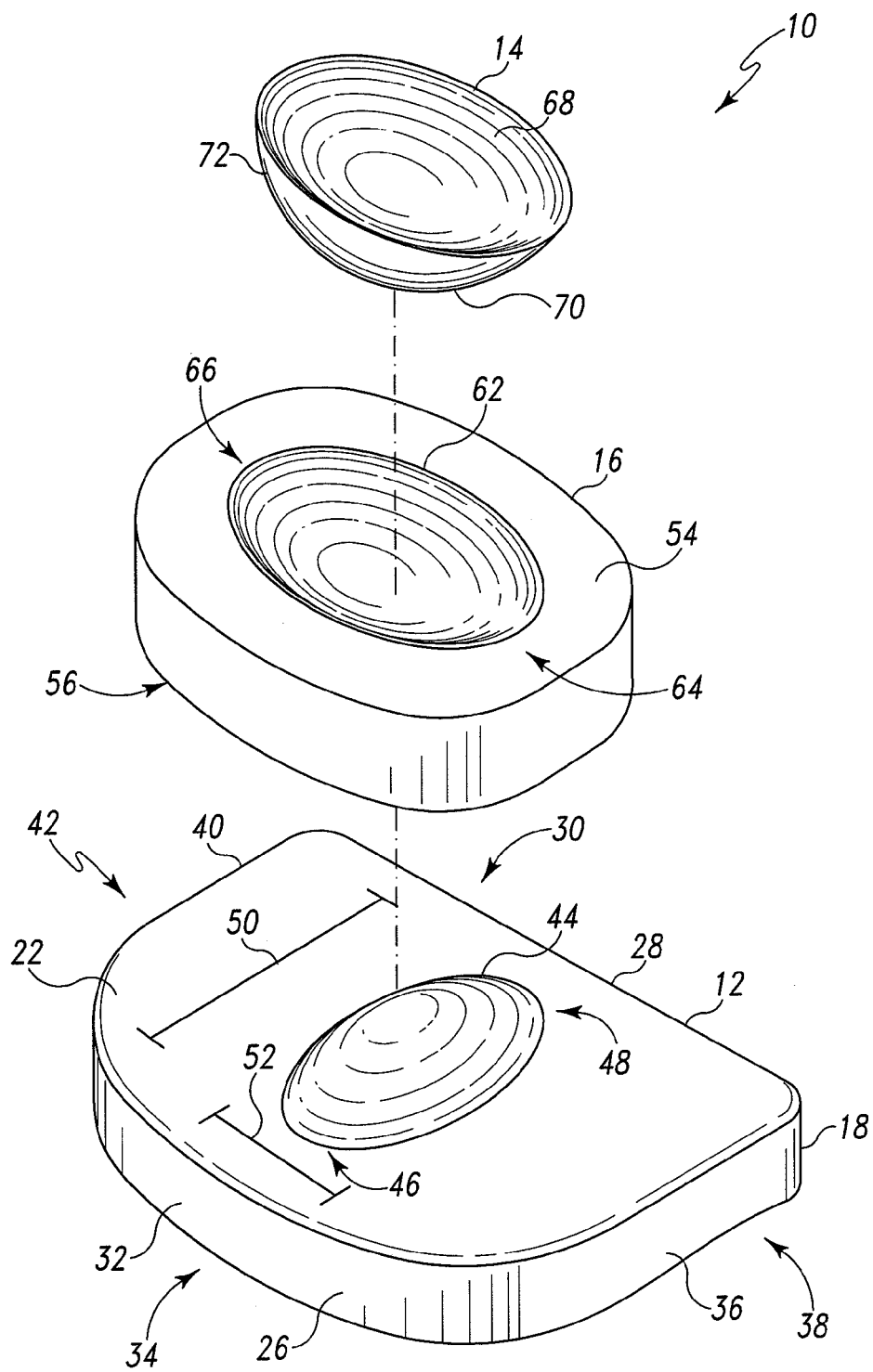
FIG. 1 is an exploded perspective view of one embodiment of a unicompartmental tibial assembly.
Figure 2:
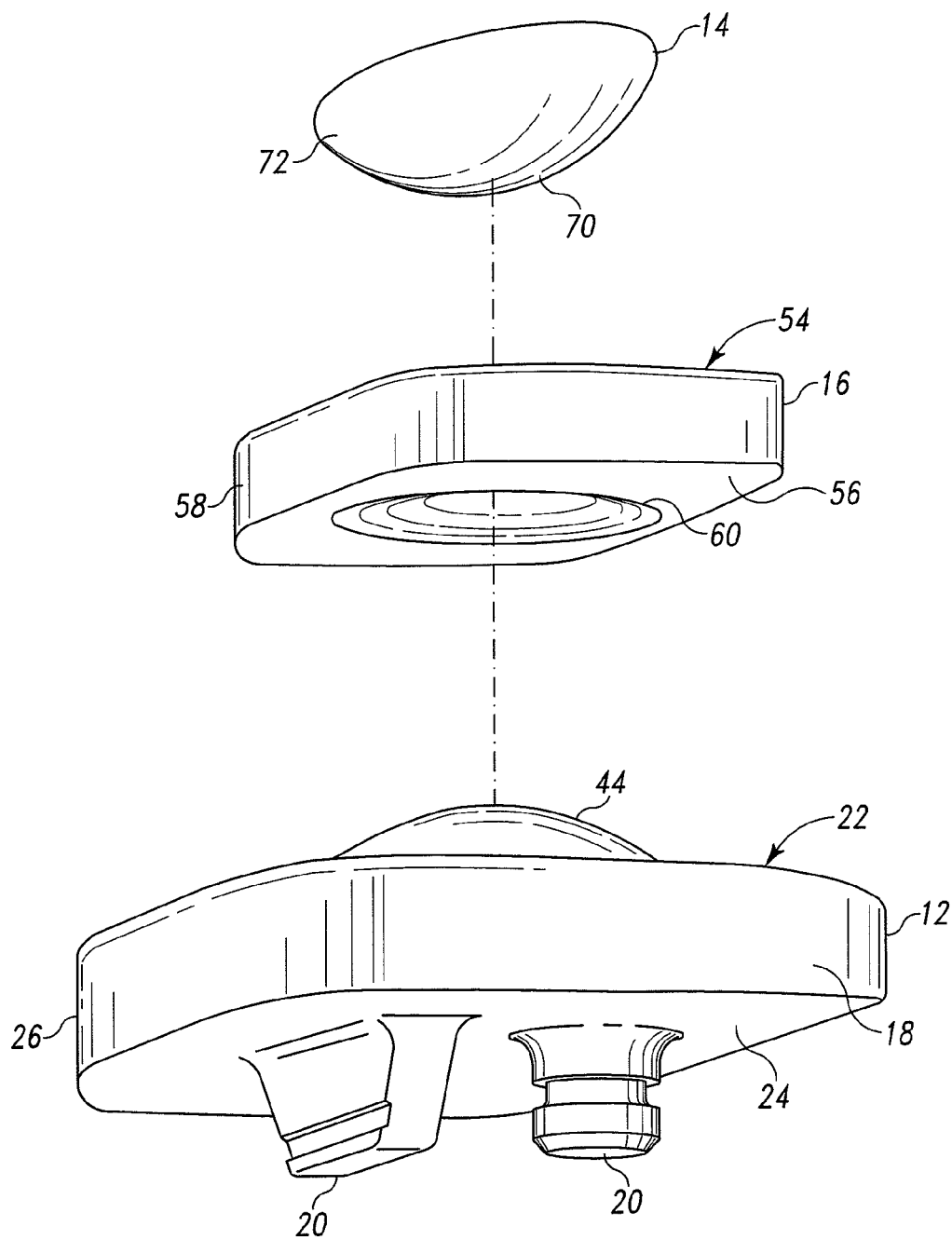
FIG. 2 is another exploded perspective view of the unicompartmental tibial assembly of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

A number of different embodiments of tibial assemblies are described below. Illustratively, the tibial assemblies are illustrated and described as unicompartmental tibial assemblies intended to replace only one of the two bearing surfaces of a patient's tibia. As such, the tibial assemblies may be used by an orthopaedic surgeon or other healthcare provider during the performance of a unicompartmental knee arthroplasty (UKA) procedure. However, it should be appreciated that the tibial assemblies described herein may also be used during the performance of a total knee arthroplasty (TKA) procedure. For example, a single tibial assembly may be used for each bearing surface of the tibia thereby improving the overall customizability of the orthopaedic implant compared to typical total knee arthroplasty implants. Additionally, the tibial assemblies described herein may be used by the surgeon or other healthcare provider during the performance of an orthopaedic surgical procedure using either conventional or minimally invasive surgical methods. Further, although the features of the tibial assemblies are described in reference to an orthopaedic knee implant, it should be appreciated that such features are applicable to other types of orthopaedic implants including, but not limited to, hip implants, shoulder implants, elbow implants, spine implants, finger implants, toe implants, wrist implants, and ankle implants.

Referring now to FIGS. 1-4, in one embodiment, a tibial assembly 10 includes a tibial tray 12, a polymer bearing hereinafter referred to as a tibial insert 14, and a platform 16 separate from the tibial tray 12 and the tibial insert 14. The tibial insert 14 is illustratively formed from a polymer material, but may be formed from other materials, such as a ceramic material, a metallic material, a bio-engineered material, or the like, in other embodiments. Similarly, the platform 16 is illustratively formed from a polymer material, but may be formed from other materials, such as a ceramic material, a metallic material, a bio-engineered material, or the like, in other embodiments. Additionally, the tibial tray 12 is illustratively formed from a metallic material, but may be formed from other materials, such as a ceramic material, a polymer material, a bio-engineered material, or the like, in other embodiments.

The tibial tray 12 is configured to be coupled to a surgically-prepared surface of the proximal end of a patient's tibia (not shown). The platform 16 is configured to be coupled with the tibial tray 12 and the tibial insert 14 as described below. The tibial tray 12 includes a base 18 and a number of anchoring devices 20, commonly referred to as stems or keels, extending downwardly therefrom. When the tibial tray 12 is coupled to the patient's tibia, the anchoring devices 18 are embedded in the tibia to thereby secure the tibial tray 12 to the patient's bone.

The base 18 has a generally "D"-shaped top profile and includes an upper surface 22 and a bottom surface 24 from which the anchoring devices 20 extend. The base 18 has a generally straight side surface 28 defining a inboard side 30 of the tibial tray 12, a generally curved side surface 32 defining an outboard side 34 of the tibial tray 12, an end surface 36 defining an anterior side 38 of the tibial tray 12, and an end surface 40 defining a posterior side 42 of the tibial tray 12. It should be appreciated that the illustrative tibial assembly 10 is but one embodiment of a tibial tray and that the features and components of the tibial assembly 10 may be used with a tibial assembly configured to replace the medial and/or lateral condyle of a patient's right tibia, as well as, the medial and/or lateral condyle of the patient's left tibia.

The tibial tray 12 has a bearing 44 extending out of the upper surface 22 of the base 20. The bearing 44 has a generally elongated convex shape, but bearings having other shapes may be used in other embodiments that allows the platform 16 to move with respect to the tibial tray 12. For example, in some embodiments, the bearing 44 may have a hypocycloid shape. The bearing 44 extends longitudinally across the upper surface 22 of the base 18 in the generally medial-lateral direction. That is, one end 46 of the bearing 20 is positioned proximate to the outboard side 34 of the tibial tray 12 with the other end 48 being positioned proximate to the inboard side 30 of the tibial tray 12. As shown in FIG. 1, it should be appreciated that the bearing 44 has a medial-lateral length 50 greater than an anterior-posterior width 52.

The platform 16 includes an upper surface 54 and a bottom surface 56 separated by a sidewall 58. The platform 16 illustratively has a generally oval-shaped top profile, but may have other configurations in other embodiments. For example, in some embodiments, the platform 16 may have a "D"-shape top profile similar to the tibial tray 12. Additionally, in some embodiments, the bottom surface 56 may be convex or otherwise curved to facilitate the movement of the platform 16 relative to the tibial tray 14 when coupled thereto.

The platform 16 includes a inferior recess 60 defined in the bottom surface 56. The recess 60 is configured to receive at least a portion of the bearing 44 of the tibial tray 12 when the platform 16 is coupled to the tray 12 as described in more detail below. As such, the recess 60 is illustratively embodied as an elongated, concave recess that extends longitudinally in a generally medial-lateral direction similar to the bearing 44 of the tibial tray 12.

The platform 16 also includes a superior recess 62 defined on the top surface 54. Similar to the inferior recess 60, the recess 62 is illustratively embodied as an elongated, concave recess that extends longitudinally in a generally anterior-posterior direction relative to the tibial tray 12. That is, when the platform 16 is coupled to the tibial tray 12 such that the bearing 44 is received by the recess 60, one end 64 of the recess 62 is positioned proximate to the anterior side 38 of the tibial tray 12 and the other end 66 of the recess 62 is positioned proximate the posterior side 42 of the tibial tray 12 as shown in FIG. 3.

The tibial insert 14 includes a top bearing surface 68 and a bottom surface 70 spaced apart, in some embodiments, by a side wall 72. The top bearing surface 68 of the tibial insert 14 is configured to contact a natural or prosthetic femoral condyle of a patient's femur. As such, during use, the patient's femur or femoral component articulates on the upper bearing surface 68. The bottom surface 70 is configured to be received by the superior recess 62 defined on the upper surface 54 of the platform 16. As such, the illustrative bottom surface 70 has a generally elongated convex shape.

During the performance of the orthopaedic surgical procedure (e.g., a UKA or TKA procedure), the tibial insert 14 is coupled to the platform 16 and the platform 16 is coupled to the tibial tray 12. The tibial insert 14 may be coupled to the platform 16 by positioning the insert 14, or portion thereof, such that the bottom surface 70 is received in the recess 66 defined on the top surface 54 of the platform. Similarly, the platform 16 may be coupled to the tibial tray 12 by positioning the platform 16 on the tibial tray 12 such that the bearing 44, or portion thereof, is received in the recess 60 defined in the bottom surface 56 of the platform 16.

Figure 3:
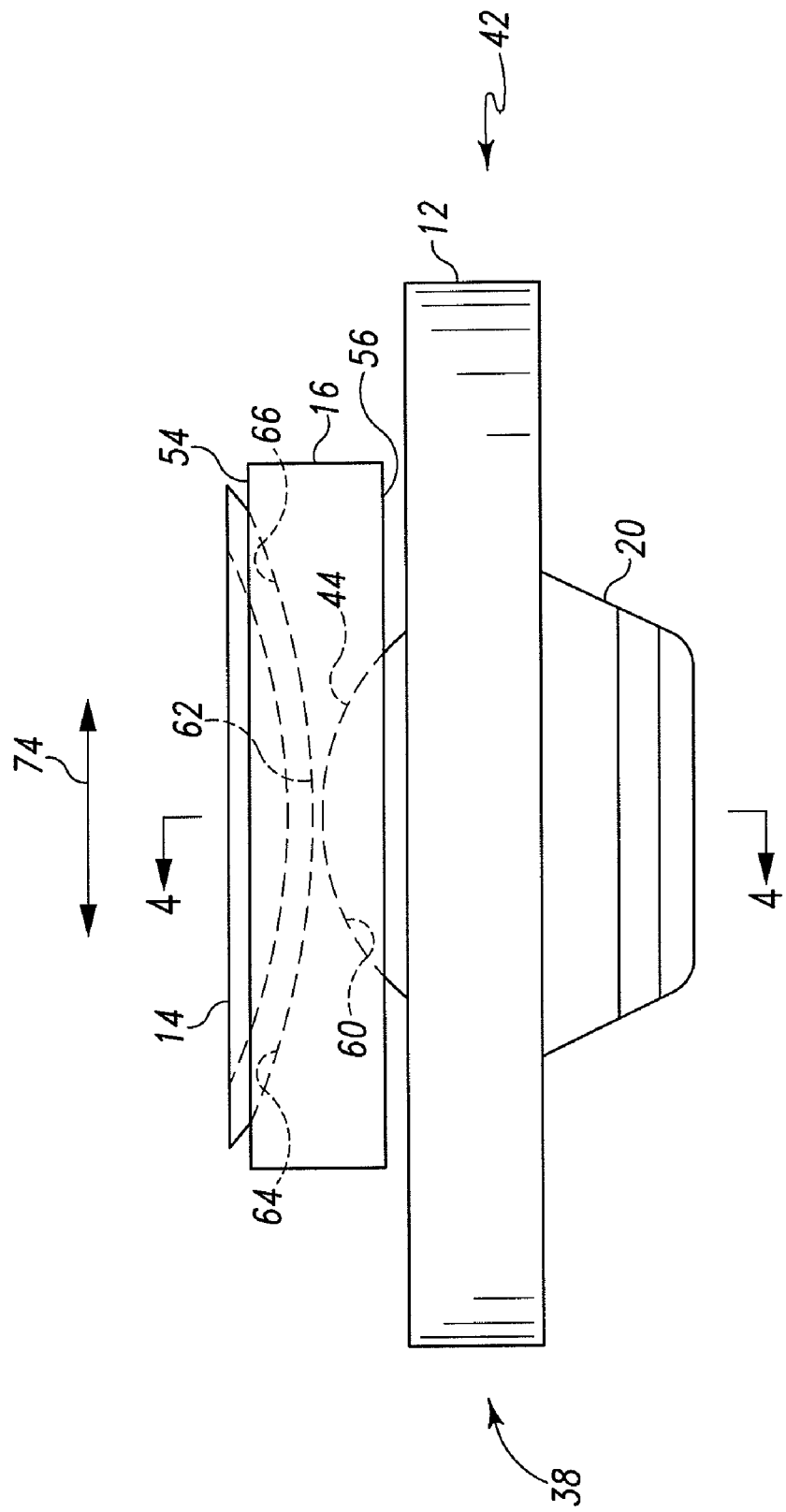
FIG. 3 is a side elevation view of the unicompartmental tibial assembly of FIG. 1 in an assembled configuration.
Figure 4:
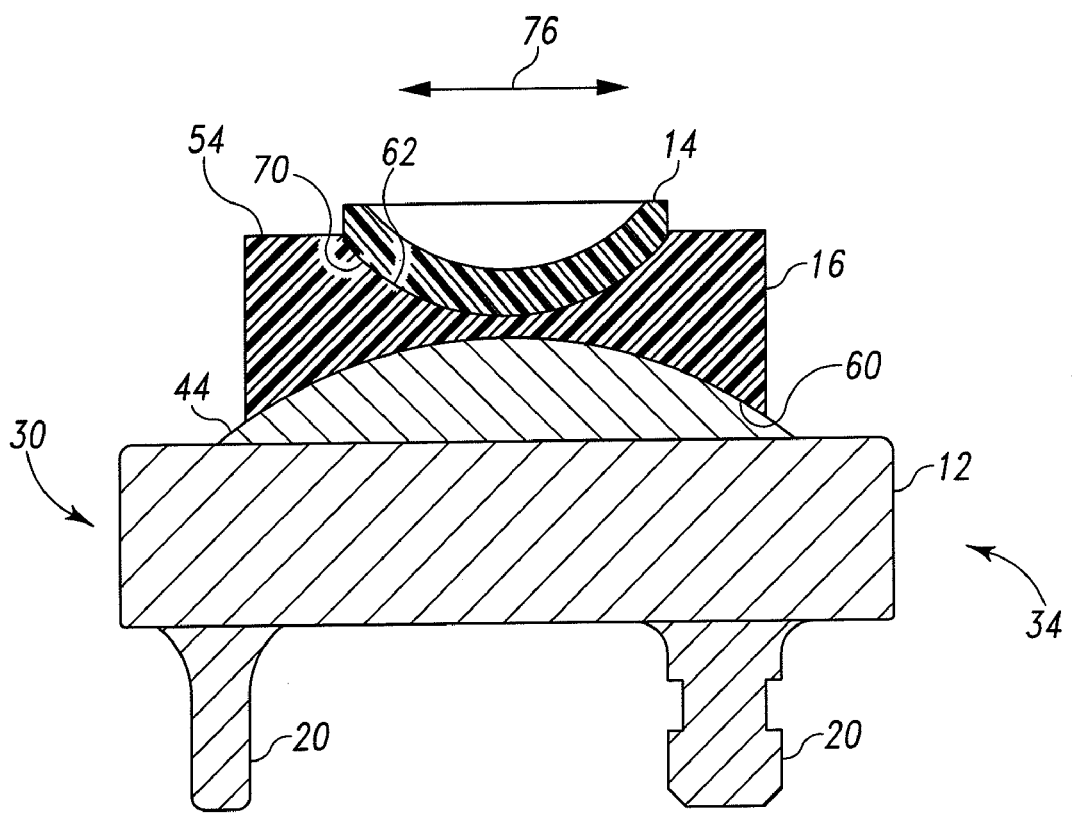
FIG. 4 is a cross-section of the unicompartmental tibial assembly of FIG. 3 taken generally along section lines 4-4.
Figure 5:
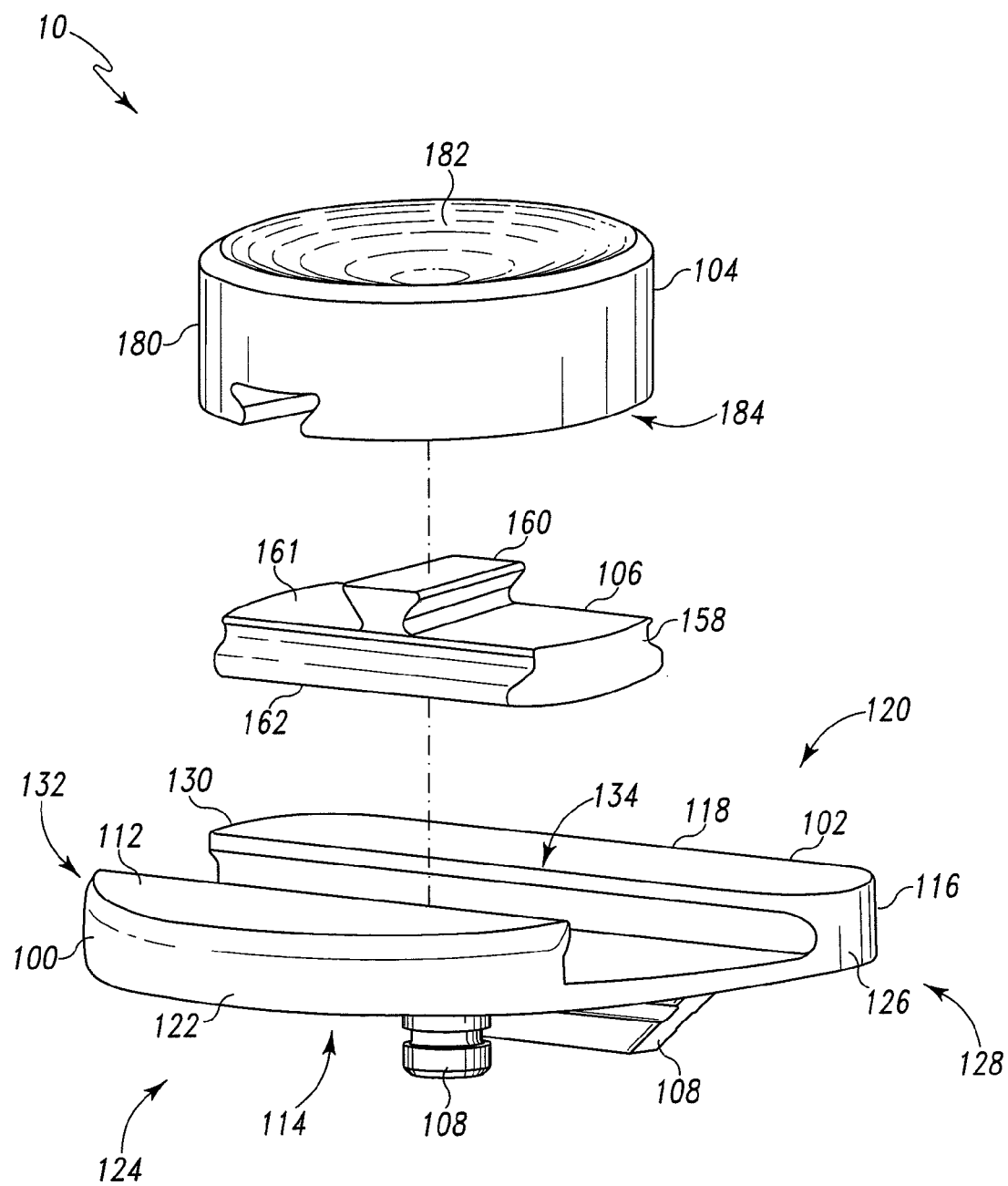
FIG. 5 is an exploded perspective view of another embodiment of a unicompartmental tibial assembly.

As shown in FIGS. 3 and 4, when the tibial tray 12, the platform 16, and the tibial insert 14 are coupled together, the tibial tray 12 is configured to move relative to the platform 16 and the platform 16 is configured to move relative to the tibial tray 12. Because the recess 66 extends longitudinally in the anterior-posterior direction, the tibial tray 12 is configured to move in the anterior-posterior direction as shown in FIG. 3 by the direction arrow 74. Similarly, because the bearing 44 and the recess 60 extend longitudinally in the generally medial-lateral direction, the platform 16 is configured to move in the generally medial-lateral direction as shown in FIG. 4 by the direction arrow 76. As such, the tibial tray 10 is configured to allow some amount of anterior-posterior movement and some amount of medial-lateral movement during normal patient use.

Referring now to FIGS. 5-10, in another embodiment, the tibial assembly 10 includes a tibial tray 102, a bearing hereinafter referred to as a tibial insert 104, and a platform 106 separate from the tibial tray 102 and the tibial insert 104. The tibial insert 104 is illustratively formed from a polymer material, but may be formed from other materials, such as a ceramic material, a metallic material, a bio-engineered material, or the like, in other embodiments. Similarly, the platform 106 is illustratively formed from a polymer material, but may be formed from other materials, such as a ceramic material, a metallic material, a bio-engineered material, or the like, in other embodiments. Additionally, the tibial tray 102 is illustratively formed from a metallic material, but may be formed from other materials, such as a ceramic material, a polymer material, a bio-engineered material, or the like, in other embodiments.

The tibial tray 102 is configured to be coupled to a surgically-prepared surface of the proximal end of a patient's tibia (not shown). The platform 106 is configured to be coupled with the tibial tray 102 and the tibial insert 140 as described below. Similar to the tibial tray 12 described above in regard to FIGS. 1-4, the tibial tray 102 includes a base 100 and a number of anchoring devices 108, commonly referred to as stems or keels, extending downwardly therefrom. As with the tibial tray 12, the base 100 of the tibial tray 102 has a generally "D"-shaped top profile and includes an upper surface 112 and a bottom surface 114 from which the anchoring devices 108 extend. The base 100 includes a generally straight side surface 118 defining a inboard side 120 of the tibial tray 102, a generally curved side surface 122 defining an outboard side 124 of the tibial tray 102, an end surface 126 defining an anterior side 128 of the tibial tray 102, and an end surface 130 defining a posterior side 132 of the tibial tray 102.

It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia. Additionally, in some embodiments, the tibial tray 102 may be embodied as a total knee tibial tray, which may be used with one or two tibial inserts 104. For example, a total knee tibial tray may be used with a single tibial insert 104 to replace either the medial or lateral condyle of the patient's knee. Alternatively, a total knee tibial tray may be used with two tibial inserts 104, each replacing one of the medial and lateral condyles of the patient's knee. In such applications, the medial and lateral tibial inserts 104 may have different characteristics and be selected based on the orthopaedic considerations associated with the respective condyle of the patient's knee.

Figure 6:
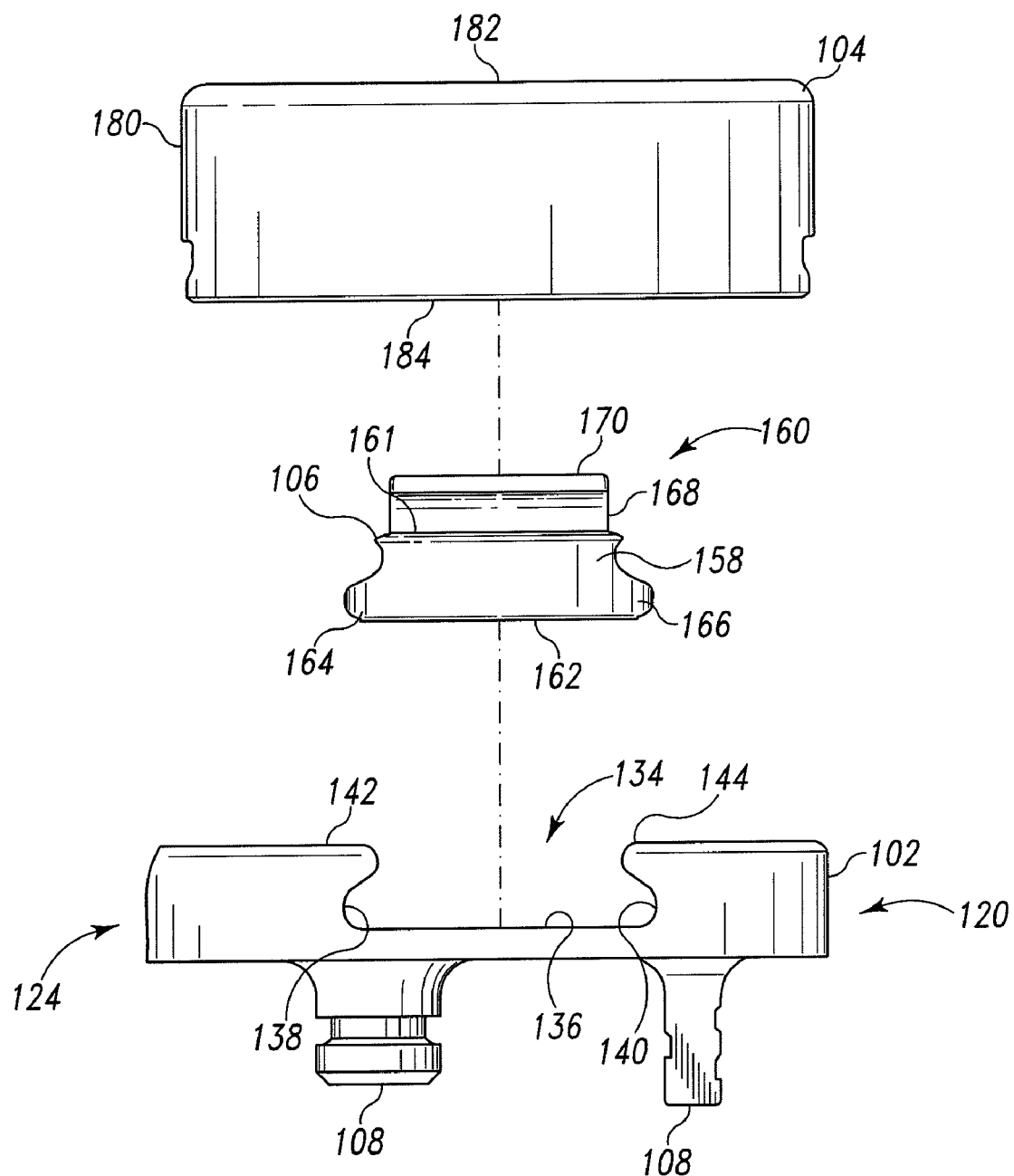
FIG. 6 is an exploded end elevation view of the unicompartmental tibial assembly of FIG. 5.

The tibial tray 102 includes a track 134 defined in the base 100. The track 134 is configured to receive a portion of the platform 106 as described below. As shown in FIG. 6, the track 134 is defined by a bottom wall 136 and side walls 138, 140. An outboard lip 142 extends from the side wall 138 and a inboard lip 144 extends from the side wall 140. In the illustrative embodiment the lips 142, 144 extend from the side walls 138, 140, respectively, an equal distance. However, in other embodiments, the lips 142, 146 may extend from the side walls 138, 140 different distances.

The outboard lip 132 includes a top surface 146 and a bottom surface 148. Similarly, the inboard lip 144 includes a top surface 150 and a bottom surface 152. In the illustrative embodiment, the top surface 146 of the lip 132 is oblique or otherwise non-parallel to the bottom surface 148 of the lip 132. Similarly, the top surface 150 of the inboard lip 144 oblique or otherwise non-parallel to the bottom surface 152 of the lip 144. However, in other embodiments, the top surfaces 146, 150 may be substantially parallel to the respective bottom surface 148, 152.

Figure 9:
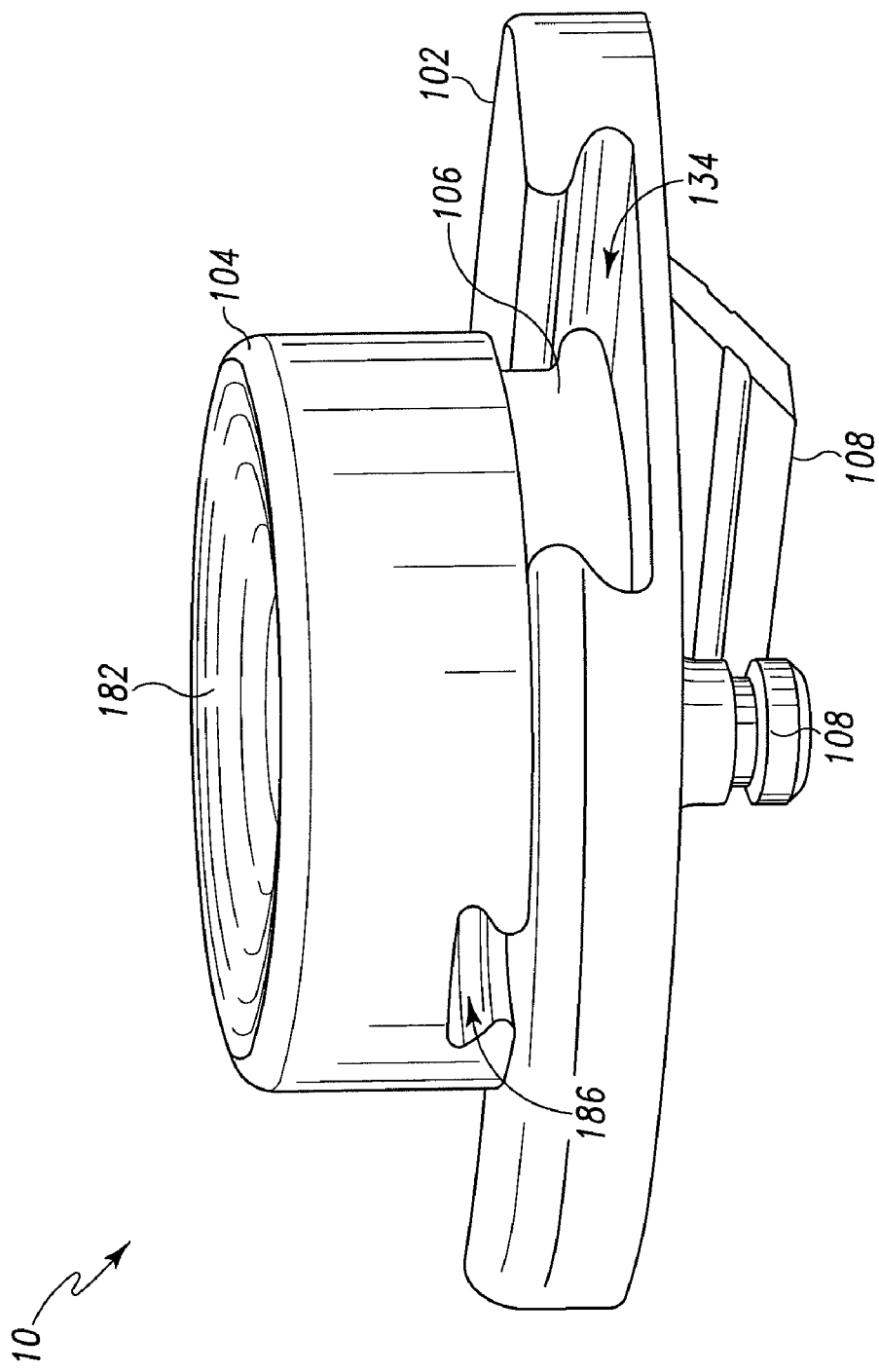
FIG. 9 is a perspective view of the unicompartmental tibial assembly of FIG. 5 in an assembled configuration.

The platform 106 includes a base 158 and a stem 160. The base 158 includes an upper surface 161, a bottom surface 162, and elongated side flanges 164, 166 The flanges 164, 166 form a rail that is received by the track 134 of the tibial tray 102 as illustrated in FIG. 9. When the platform 106 is coupled to the tibial tray 102, the bottom surface 162 of the platform 106 contacts or is otherwise adjacent to the bottom surface 136 of the track 134. Additionally, the side flanges 164, 166 are positioned in the regions defined under the lips 142, 144, which retrain the platform 106 in the track 134 thereby preventing the platform 106 from lifting off the tibial tray 102.

Figure 7:
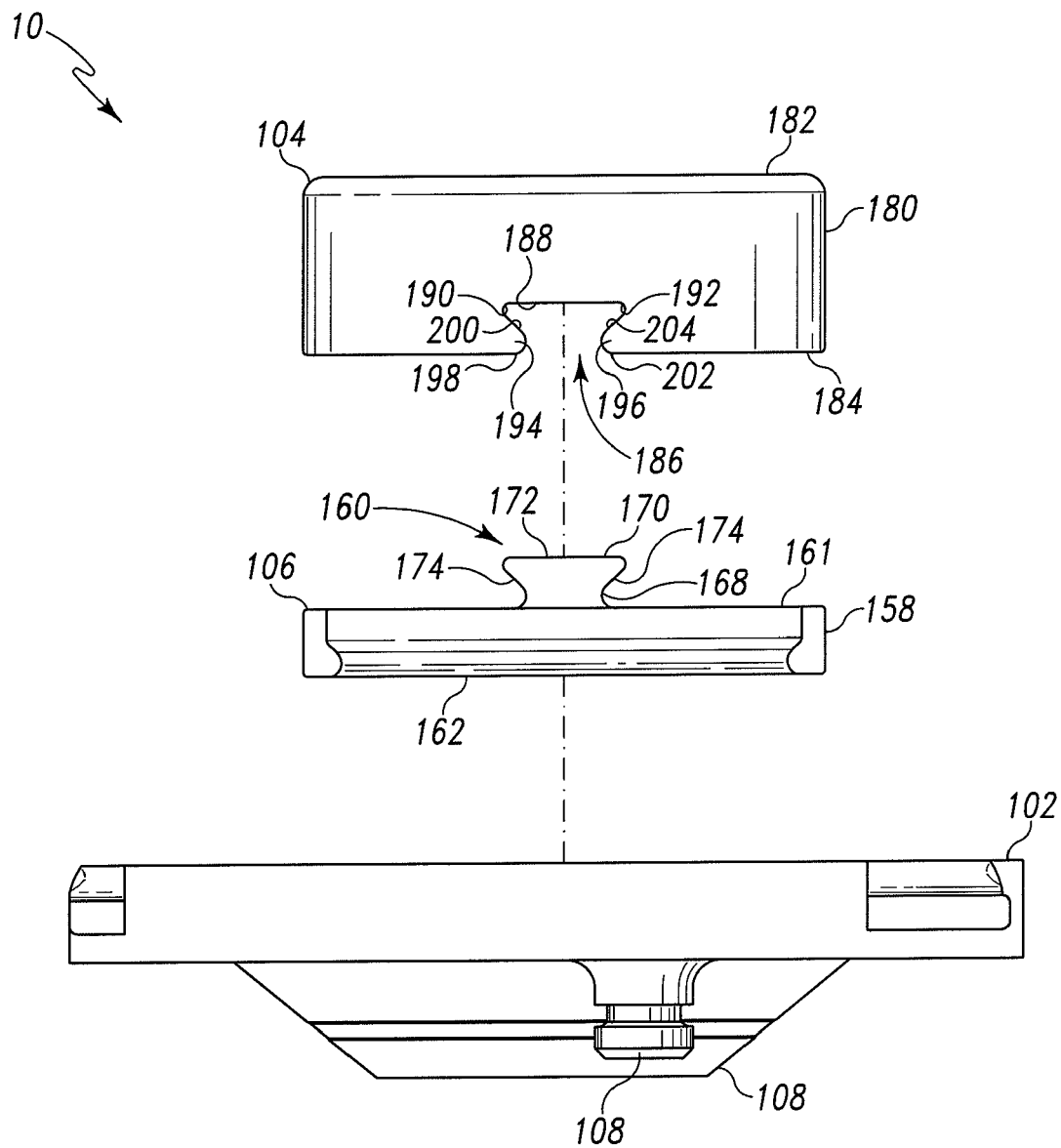
FIG. 7 is an exploded side elevation view of the unicompartmental tibial assembly of FIG. 5.
Figure 8:
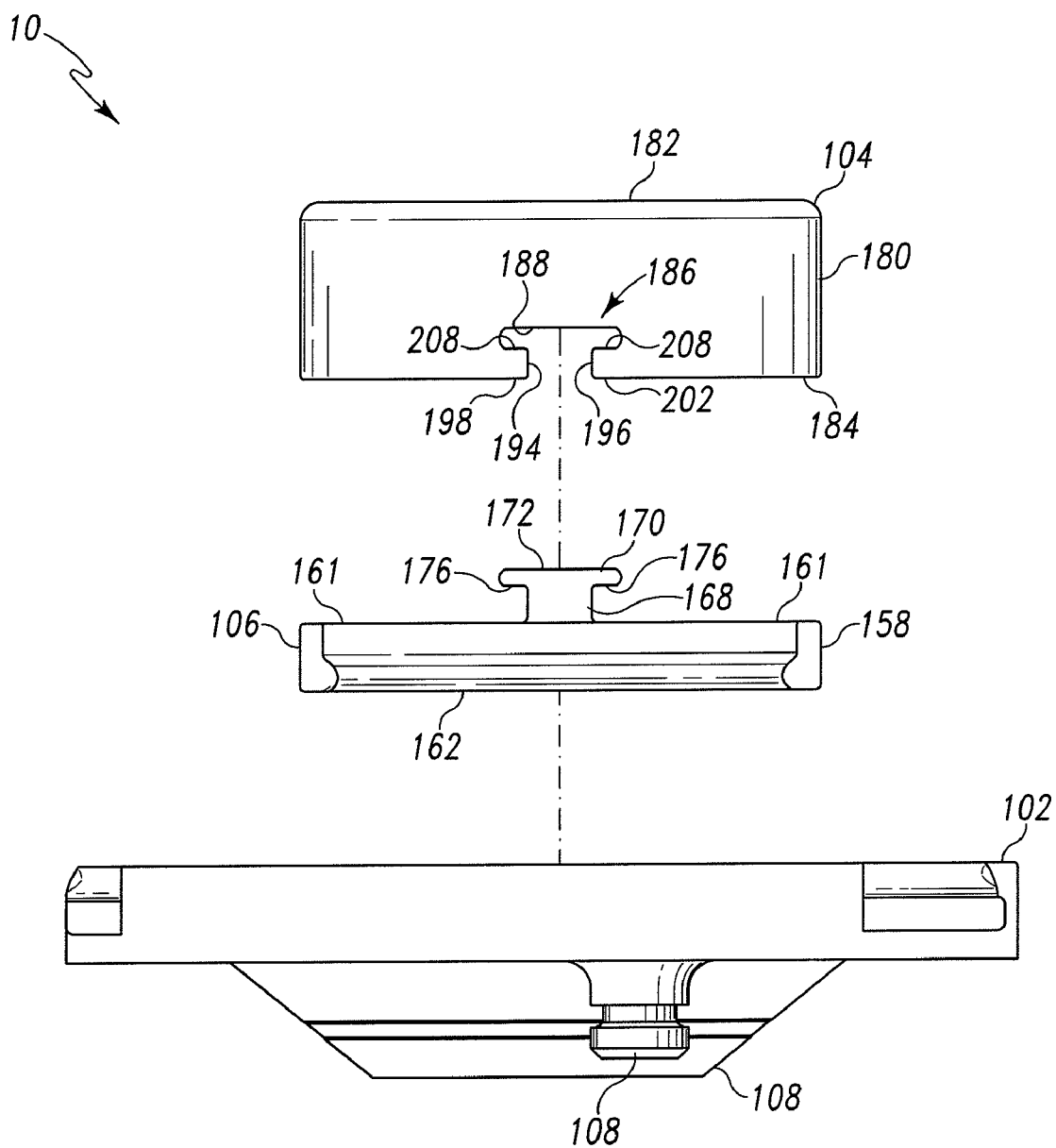
FIG. 8 is an exploded side elevation view of another embodiment of the unicompartmental tibial assembly of FIG. 5.

The stem 160 includes a neck 168 and an elongated flange 170 defined at a end of the neck 168. The flange 170 forms a rail that is received by the tibial insert 102 as discussed below. The flange 170 is illustratively positioned orthogonally relative to the flange 162, 164 of the base 158, but may have other relative orientations in other embodiments. The flange 170 includes a top surface 172 and a bottom surface 174. In the illustrative embodiment of FIGS. 5-7, the bottom surface 174 is oblique or otherwise not parallel to the top surface 172. However, as illustrated in FIG. 8, the flange 170 may include a bottom surface 176 that is substantially parallel to the top surface 172 in other embodiments.

The tibial insert 14 includes a base 180 having an upper bearing surface 182 and a bottom surface 184. The upper bearing surface 182 is configured to contact or otherwise support a natural or prosthetic femoral condyle of a patient's femur. During use, the patient's femur or femoral component articulates on the upper bearing surface 184. The base 180 includes a track 186. The track 186 is configured to receive the stem 160 of the platform 106 as described below. As shown in FIG. 7, the track 186 is defined by a bottom wall 188 and side walls 190, 192. An outboard lip 194 extends from the side wall 190 and a inboard lip 196 extends from the side wall 192. In the illustrative embodiment the lips 194, 196 extend from the side walls 190, 192, respectively, an equal distance. However, in other embodiments, the lips 194, 196 may extend from the side walls 190, 192 different distances.

The outboard lip 194 includes a top surface 198 and a bottom surface 200. Similarly, the inboard lip 196 includes a top surface 202 and a bottom surface 204. In the illustrative embodiment, the top surface 198 of the lip 194 is oblique or otherwise non-parallel to the bottom surface 200 of the lip 194. Similarly, the top surface 202 of the inboard lip 196 is oblique or otherwise non-parallel to the bottom surface 204 of the lip 196. However, as illustrated in FIG. 8, in embodiments wherein the flange 170 of the platform 106 includes substantially parallel surfaces 172, 176, the lips 194, 198 may include bottom surfaces 206, 208, respectively, that are substantially parallel to the respective top surfaces 198, 202 of the lips 194, 198 such that the track 186 is configured to receive the stem 160.

During the performance of the orthopaedic surgical procedure (e.g., a UKA or TKA procedure), the tibial tray 102, platform 106, and tibial insert 104 are coupled together as illustrated in FIG. 9. The platform 106 may be coupled to the tibial tray 102 by inserting the base 158 into the track 134 of the tibial tray 102. To do so, the platform 106 may be positioned such that the flanges 164, 166 are received in the regions defined under the lips 142, 144. Once the base 158 is received in the track 134, the platform 106 may be slid or otherwise moved along the track 134. Similarly, the tibial insert 104 may be coupled to the platform 106 by inserting the stem 160 of the platform 106 into the track 186 of the tibial insert 104. To do so, the tibial insert 104 may be positioned such that the flange 160 of the platform 106 is received by the regions defined under the lips 194, 198 of the tibial tray 104. Once stem 160 is received in the track 186, the tibial insert 104 may be moved relative to the platform 106 by sliding the tibial insert 104 across the flange 170 of the platform 106.

Figure 10:
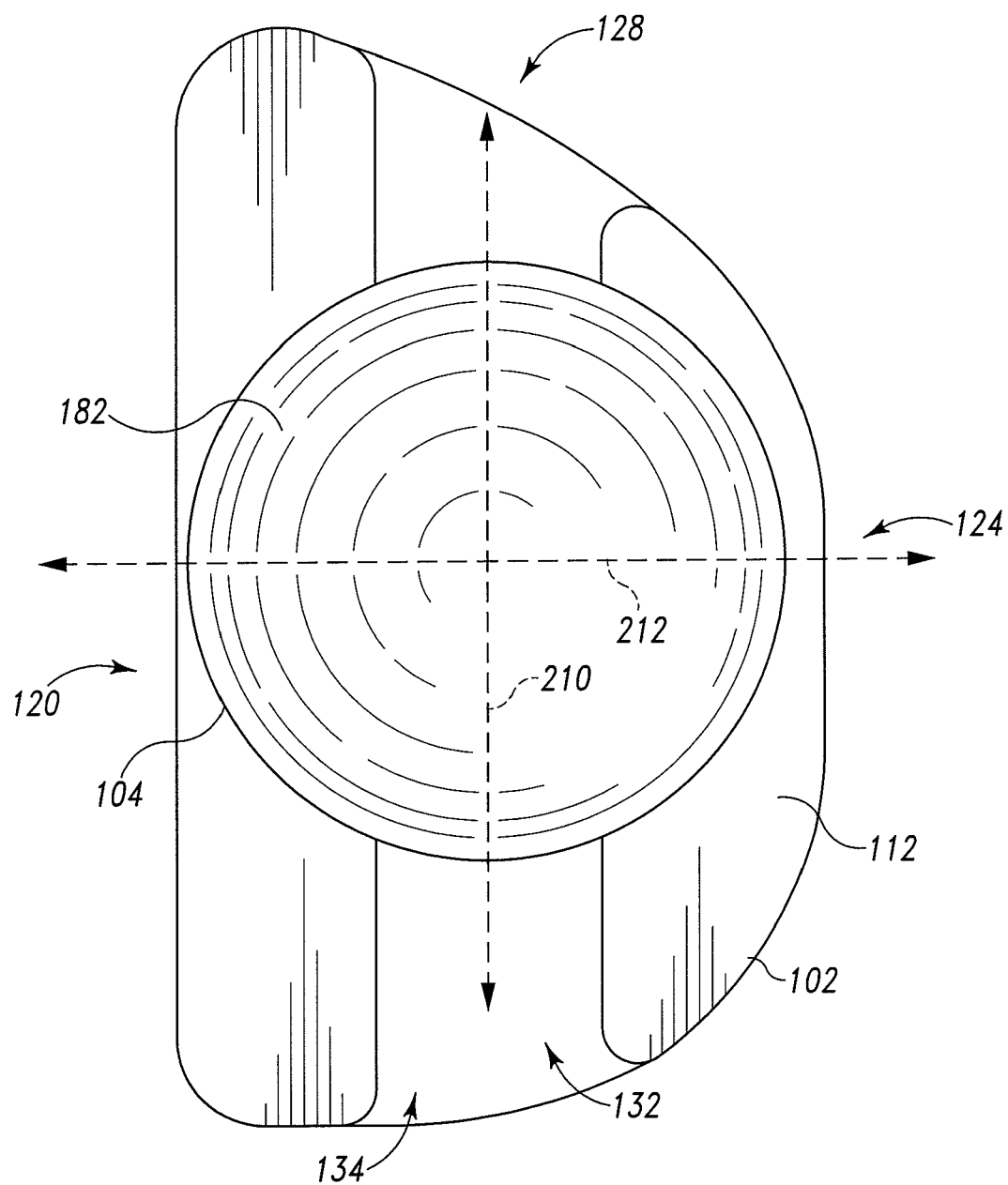
FIG. 10 is a plan view of the unicompartmental tibial assembly of FIG. 9.
Figure 11:
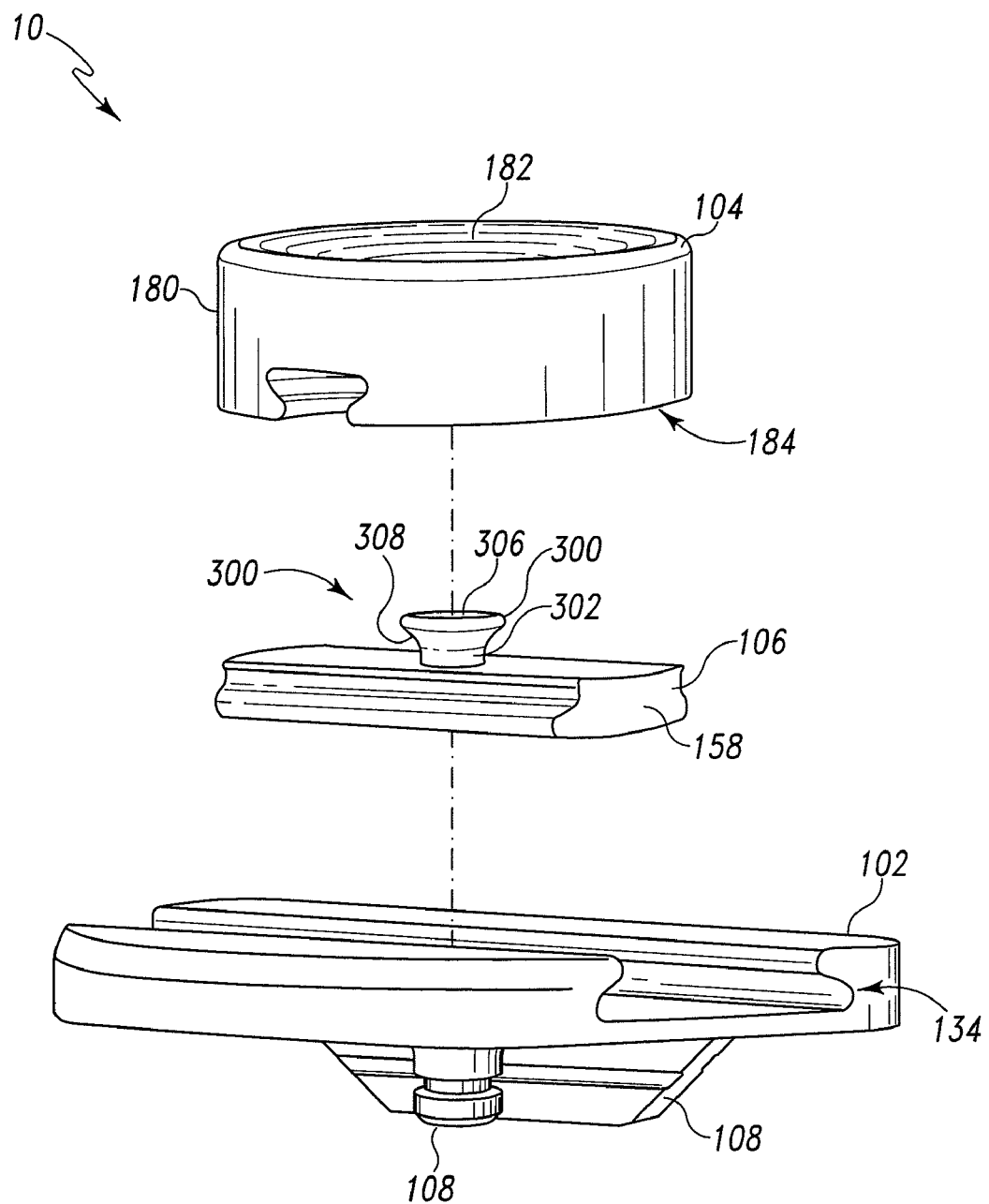
FIG. 11 is an exploded perspective view of another embodiment of a unicompartmental tibial assembly.
Figure 12:
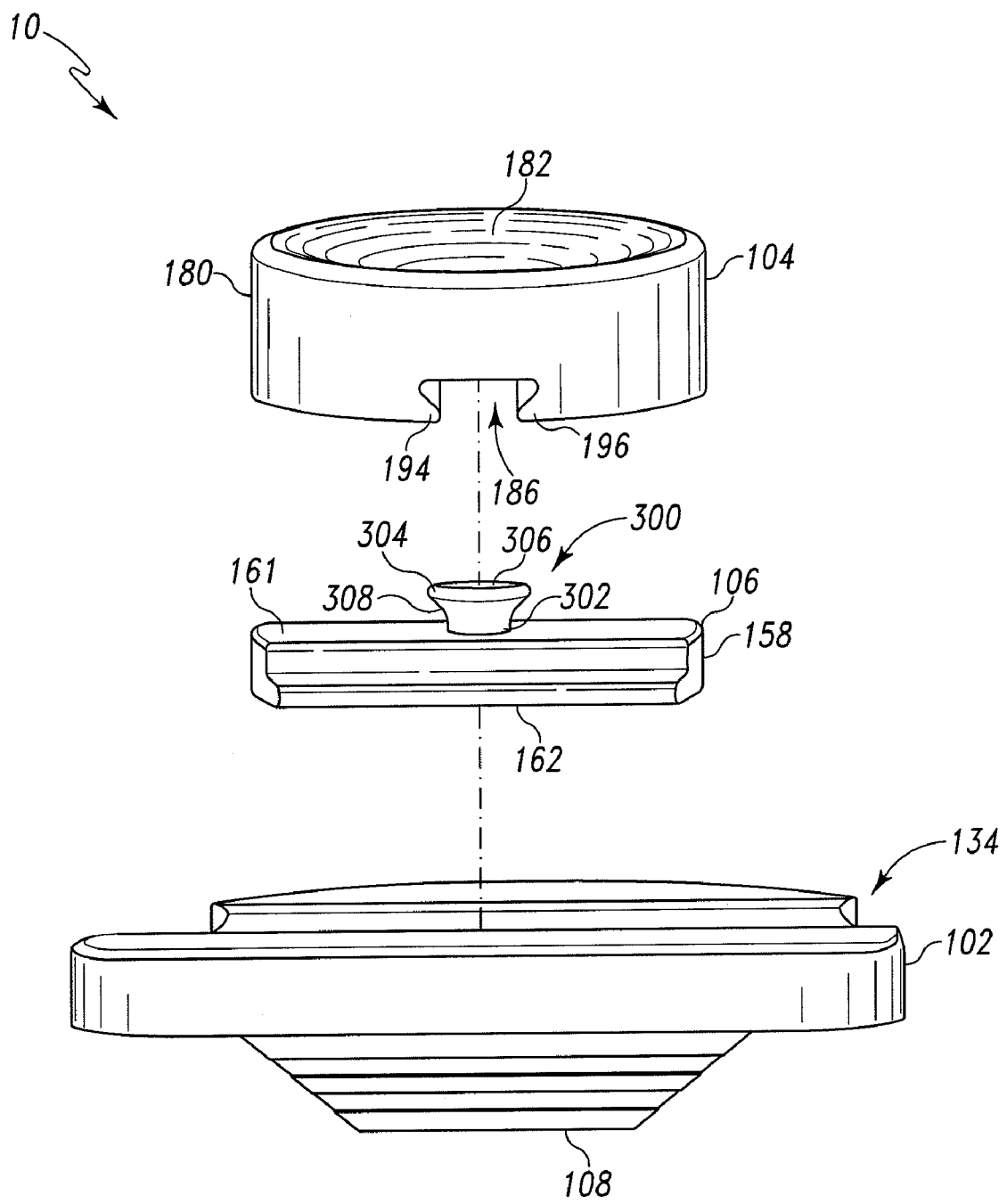
FIG. 12 is an exploded side elevation view of the unicompartmental tibial assembly of FIG. 11.

During patient use, the platform 106 moves along the track 134 of the tibial tray 102 in a generally anterior-posterior direction as indicated by direction arrow 210 in FIG. 10. In addition, the tibial insert 104 moves along the flange 170 of the platform 106 in a medial-lateral or lateral medial direction as indicated by direction arrow 212. As such, in use, the tibial insert 104 is configured to move anteriorly-posteriorly and/or medially-laterally with respect to the tibial tray 104.

Referring now to FIGS. 11-14, in another embodiment, the platform 106 may include a stem 300 in place of the stem 160 described above in regard to FIGS. 5-10. The stem 300 extends upwardly from the base 158 of the platform 106. The stem 300 includes a neck 302 and a flange 304 defined at an end of the neck 302. The illustrative flange 304 has a generally elliptical or circular top profile but may have other configuration in other embodiments. The flange 304 includes an top surface 306 and a bottom surface 308. In the embodiment illustrated in FIGS. 11-14, the bottom surface 308 is oblique or otherwise not parallel to the upper surface 306 such that the flange 304 may be received in the track 186. Additionally, the bottom surface 308 may be oblique or otherwise not parallel to the bottom surface 188 of the track 186 of the tibial insert 104. However, in embodiments wherein the track 186 is defined by lips 194, 196 having parallel top surfaces 198, 202 and bottom surfaces 206, 208, respectively (See FIG. 8), the flange 304 may include a bottom surface that is parallel to the top surface 306 such that the flange 304 may be received in the track 186.

Figure 13:
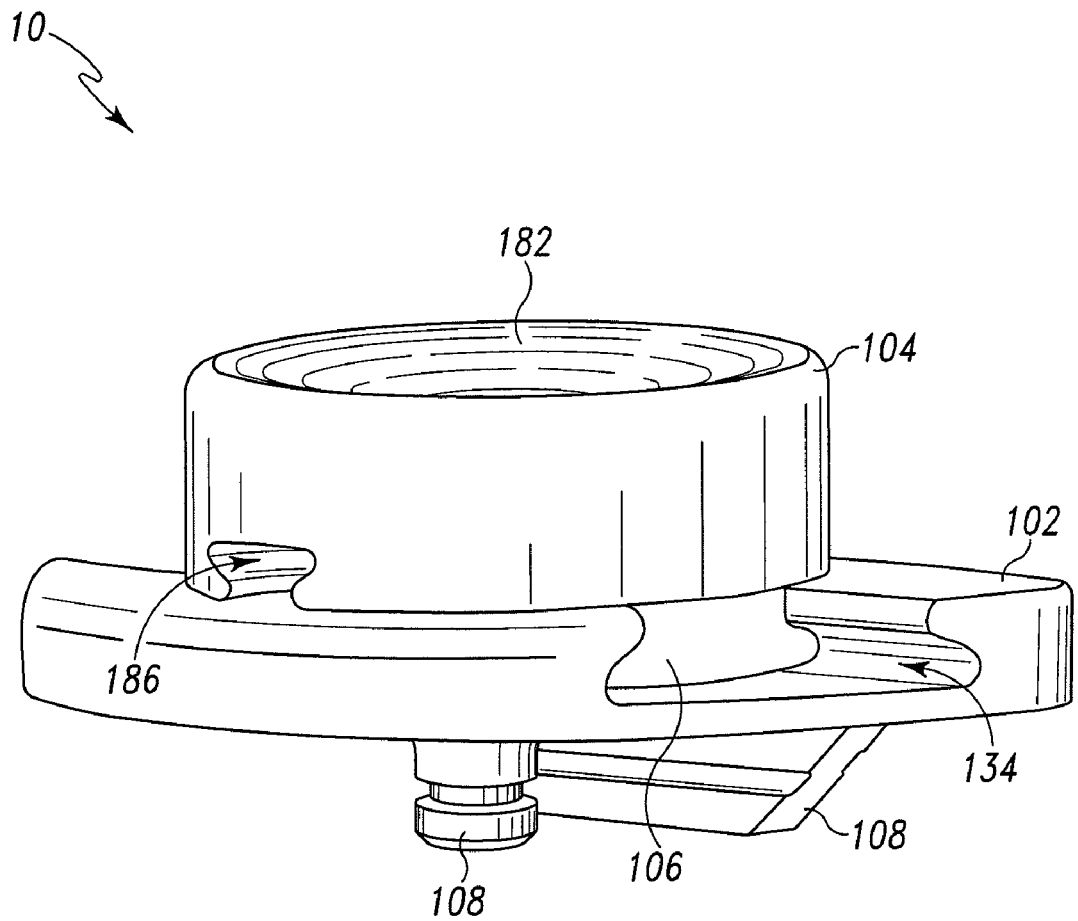
FIG. 13 is a perspective view of the unicompartmental tibial assembly of FIG. 11 in an assembled configuration.

As described above, the tibial tray 102, platform 106, and tibial insert 104 are coupled together during the performance of the orthopaedic surgical procedure (e.g., a UKA or TKA procedure) as illustrated in FIG. 13. Again, the platform 106 may be coupled to the tibial tray 102 by inserting the base 158 into the track 134 of the tibial tray 102 in the manner described above in regard to FIGS. 5-10. The tibial insert 104 may be coupled to the platform 106 by inserting the stem 300 of the platform 106 into the track 186 of the tibial insert 104. To do so, the tibial insert 104 may be positioned such that the flange 304 of the platform 106 is received by the regions defined under the lips 194, 198 of the tibial insert 104. Once the stem 300 is received in the track 186, the tibial insert 104 may moved relative to the platform 106 by sliding the tibial insert 104 across the flange 304 of the platform 106.

Figure 14:
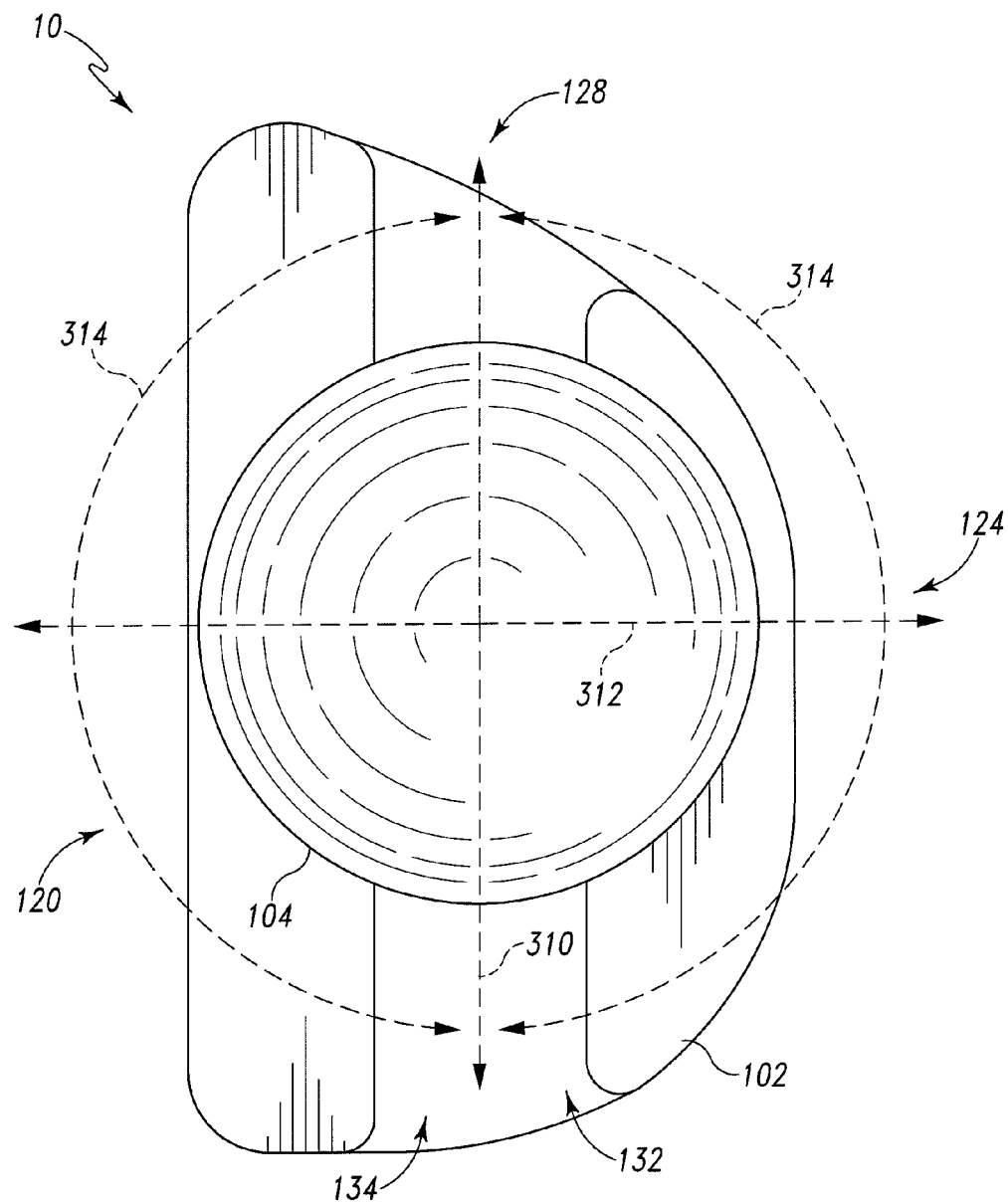
FIG. 14 is a plan view of the unicompartmental tibial assembly of FIG. 11.
Figure 15:
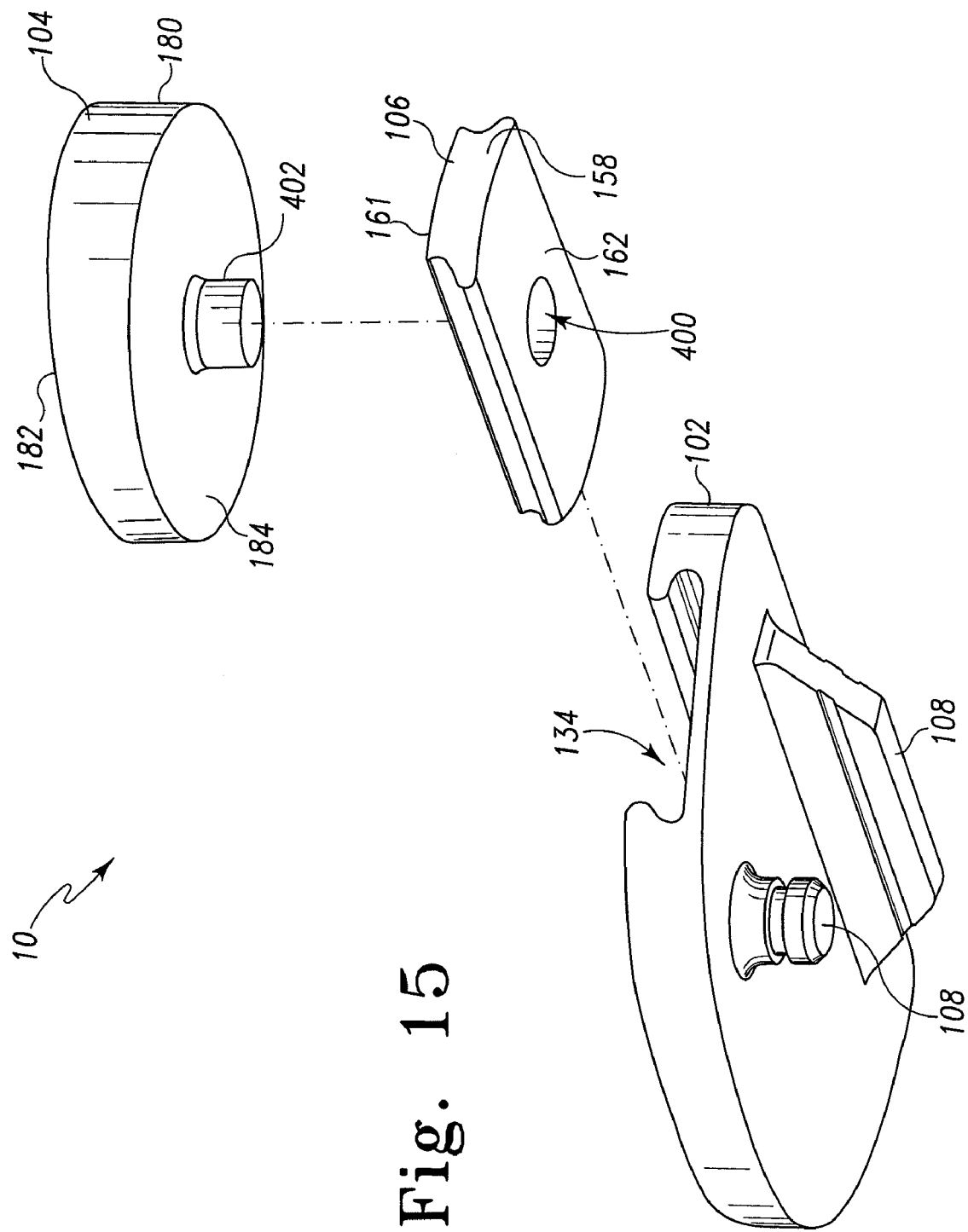
FIG. 15 is an exploded perspective view of another embodiment of a unicompartmental tibial assembly.
Figure 16:
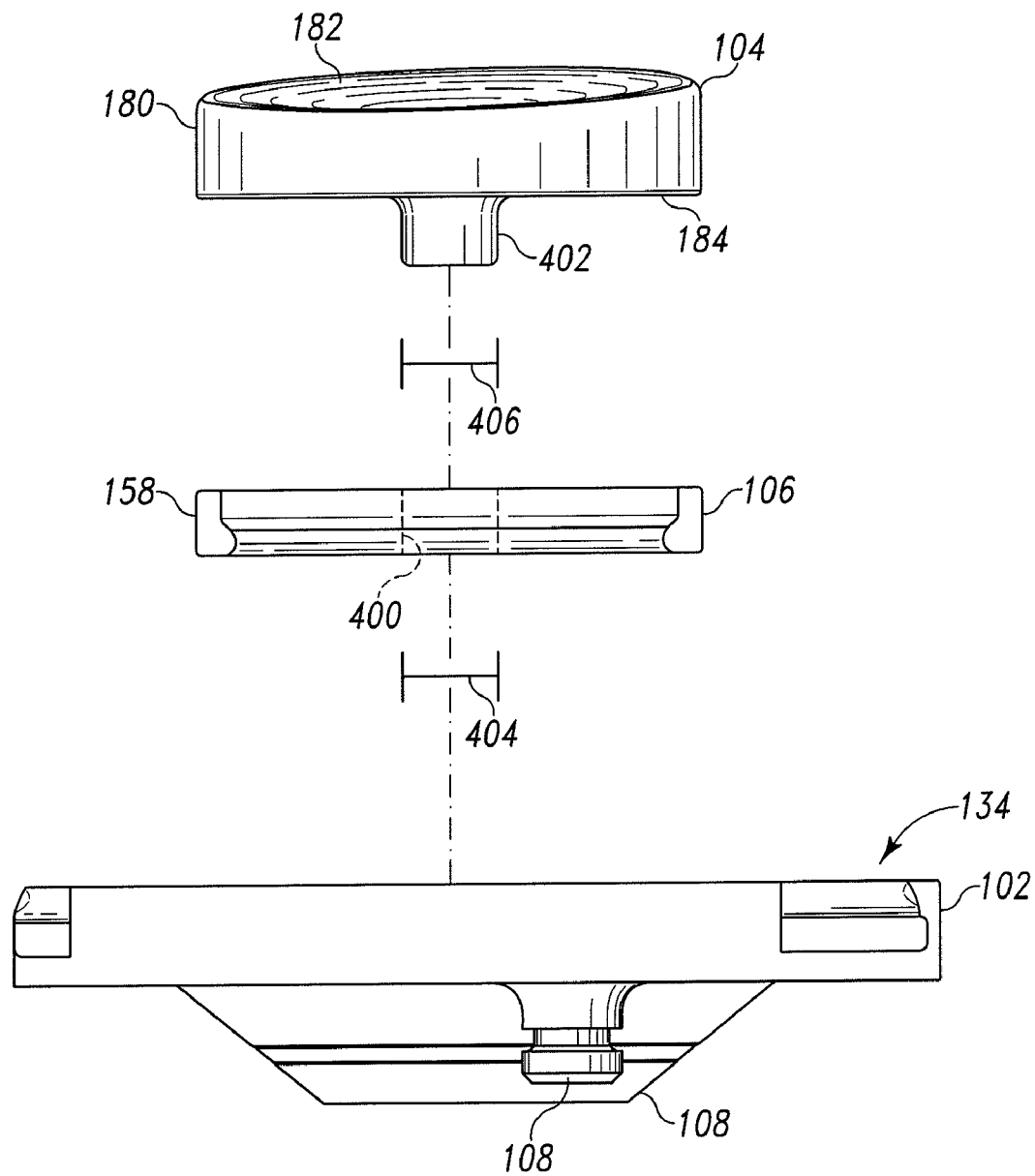
FIG. 16 is an exploded side elevation view of the unicompartmental tibial assembly of FIG. 15.

During patient use, the platform 106 moves along the track 134 of the tibial tray 102 in an anterior-posterior or posterior-anterior direction as indicated by direction arrow 310 in FIG. 14. In addition, the tibial insert 104 moves along the flange 304 of the platform 106 in a medial-lateral or lateral-medial direction as indicated by direction arrow 312. Further, because the flange 304 has a generally circular top profile shape, the tibial insert 104 may rotate about the stem 300 of the platform 16 as indicated by direction arrows 314. As such, in use, the tibial insert 104 is configured to move generally anteriorly-posteriorly, medially-laterally, and rotational with respect to the tibial tray 104.

Referring now to FIGS. 15-18, in another embodiment, the platform 106 may include an aperture 400 in place of the stem 160 described above in regard to FIGS. 5-10. The aperture 400 is defined in the upper surface 161 of the base 158 and extends downwardly through the base 158 to the bottom surface 162 of the platform 106. However, in other embodiments, the aperture 400 may not extend completely through the base 158 (i.e., the aperture 400 may not extend from the upper surface 161 to the bottom surface 162). The aperture 400 is illustratively cylindrical in shape with a circular cross-section, but may have other configurations in other embodiments.

In embodiments wherein the platform 106 includes the aperture 400, the tibial insert 102 includes a stem 402 in place of the track 186. The stem 402 extends downwardly from the bottom surface 184 of the base 180 of the tibial insert 104. Illustratively, the stem 402 is generally cylindrical in shape, but stems having other shapes may be used in other embodiments. The stem 402 is configured to be received by the aperture 400. For example, the illustrative stem 402 has a diameter 404 substantially equal to or less than the diameter 406 of the aperture 400 such that the stem 402 may be inserted therein.

Figure 17:
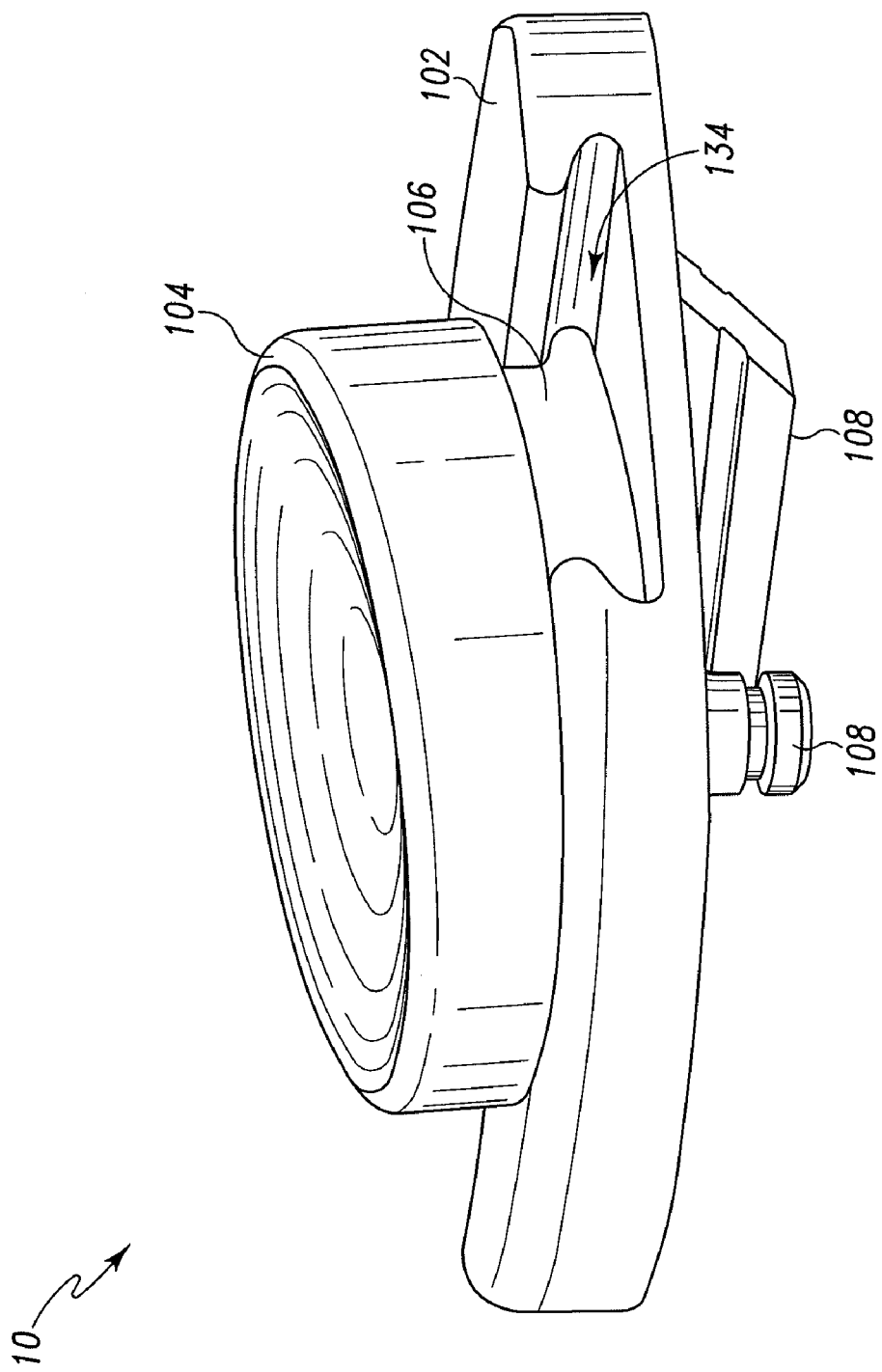
FIG. 17 is a perspective view of the unicompartmental tibial assembly of FIG. 15 in an assembled configuration.
Figure 18:
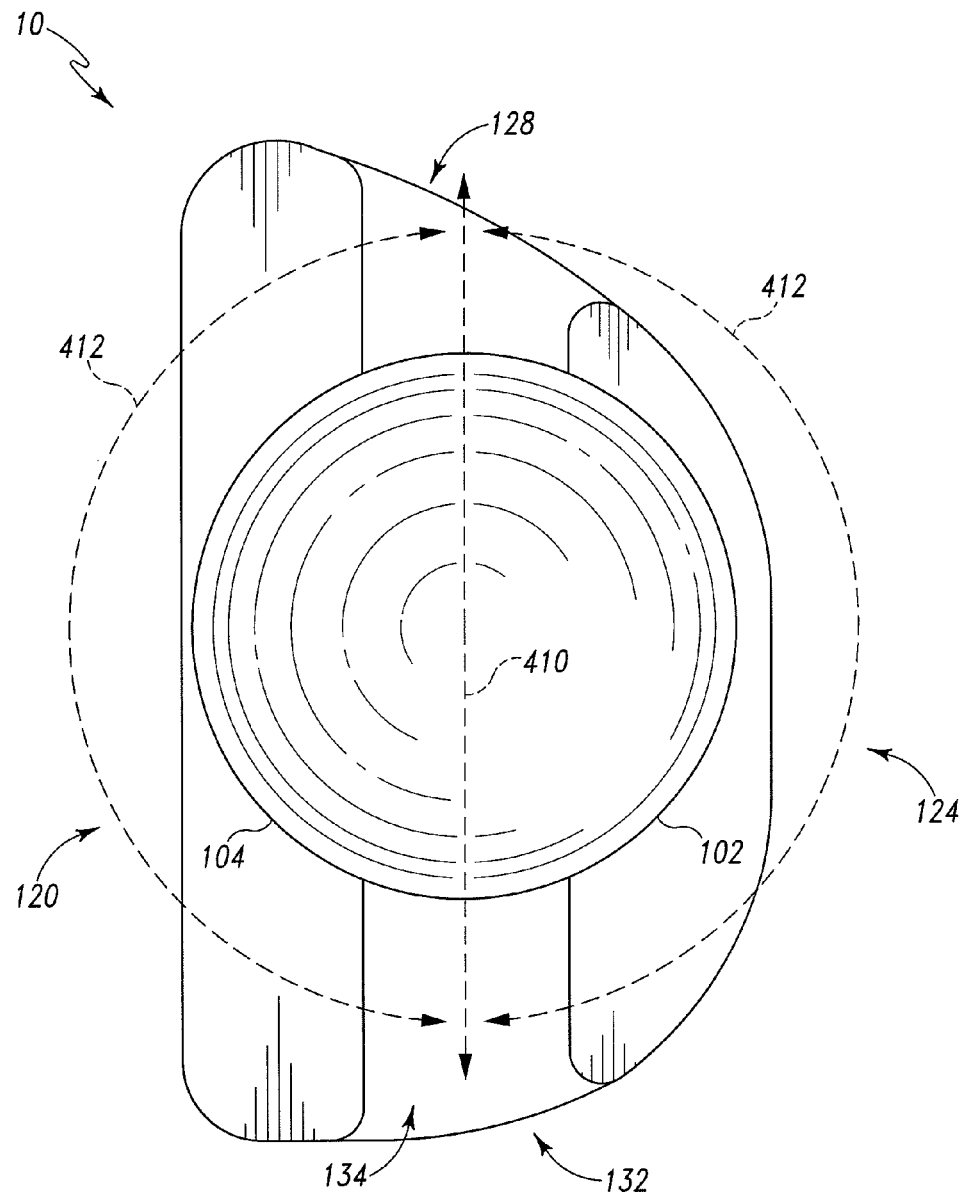
FIG. 18 is a plan view of the unicompartmental tibial assembly of FIG. 15.

As described above, the tibial tray 102, platform 106, and tibial insert 104 are coupled together during the performance of the orthopaedic surgical procedure (e.g., a UKA or TKA procedure) as illustrated in FIG. 17. Again, the platform 106 may be coupled to the tibial tray 102 by inserting the base 158 into the track 134 of the tibial tray 102 in the manner described above in regard to FIGS. 5-10. The tibial tray 102 may be coupled to the platform 106 by inserting the stem 402 of the tibial insert 104 into the aperture 400 of the platform 106. Once the stem 400 is received in the aperture 402, the tibial insert 104 may be moved relative to the platform 106 by rotating the tibial tray 104 about an axis defined by the stem 402.

During patient use, the platform 106 moves along the track 134 of the tibial tray 102 in an anterior-posterior or posterior-anterior direction as indicated by direction arrow 410 in FIG. 14. Because the aperture 400 and the stem 402 are substantially cylindrical in shape, the tibial insert 104 may also rotate about an axis defined by the stem 402 as indicated by direction arrows 412. In addition, in embodiments in which the stem 402 has a sufficiently smaller diameter 406 compared to the diameter 404 of the aperture 400, the tibial insert 104 may be configured to move some amount in a medial-lateral or lateral medial direction. As such, in use, the tibial insert 104 is configured to move generally anteriorly-posteriorly and rotationally with respect to the tibial tray 104.

Figure 19:
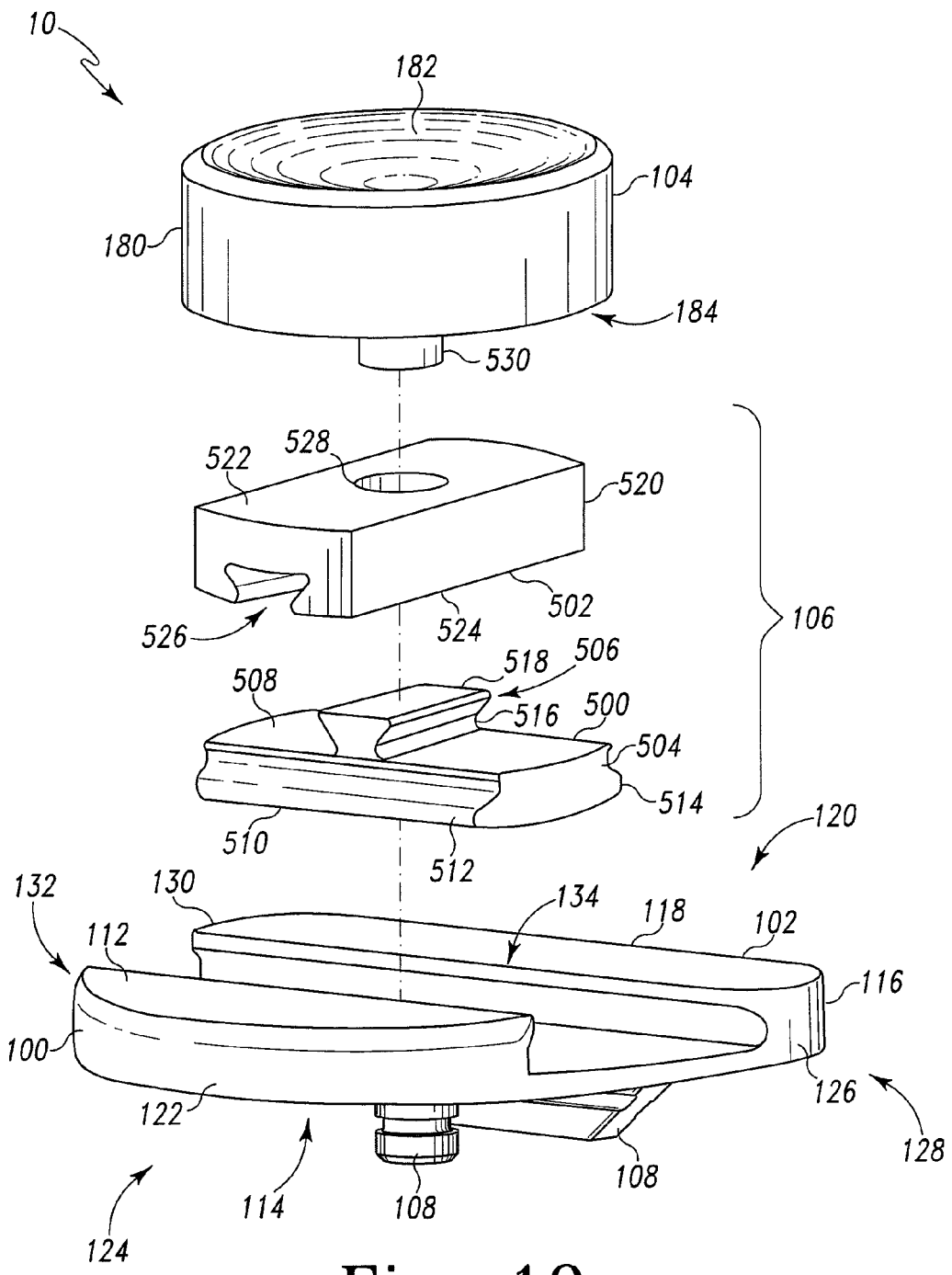
FIG. 19 is an exploded perspective view of another embodiment of a unicompartmental tibial assembly.

Referring now to FIG. 19, in some embodiments, the platform 106 may be multi-pieced. That is, the platform 106 may be embodied as two or more separate platforms, each couplable to another platform and movable relative to the other platform. For example, as illustrated in FIG. 19, the platform 106 may be embodied as a platform 500 and a platform 502. The illustrative platform 500 is substantially similar to the platform 106 illustrated in and described above in regard to FIGS. 5-7. The platform 500 includes a base 504 and a stem 506. The base 504 includes an upper surface 508, a bottom surface 510, and elongated side flanges 512, 514. The flanges 512, 514 form a rail that is received by the track 134 of the tibial tray 102. The stem 506 includes a neck 516 and an elongated flange 518 defined at a end of the neck 516. The flange 518 forms a rail that is received by the platform 502 as discussed below.

The platform 502 includes a base 520 having an upper surface 522 and bottom surface 524. The base 520 includes a track 526 define in the bottom surface 524. The tack 526 is substantially similar to the track 186 of the tibial insert 14 illustrated in and described above in regard to FIGS. 5-7. The track 526 is configured to receive the stem 506 of the platform 500. The base 520 also includes an aperture 528 defined on the upper surface 522. The aperture 528 is configured to receive a stem 530 of the tibial insert 104.

In illustrative embodiment, the tibial insert 104 is substantially similar to the tibial insert 104 illustrated in and described above in regard to FIGS. 15-18. That is, the tibial insert 14 includes a stem 530 in place of the track 186. The stem 530 is substantially similar to the stem 402 described above and extends downwardly from the bottom surface 184 of the base 180 of the tibial insert 104. Illustratively, the stem 530 is generally cylindrical in shape, but stems having other shapes may be used in other embodiments. As discussed above, the stem 530 is configured to be received by the aperture 528 of the platform 502.

During the performance of the orthopaedic surgical procedure (e.g., a UKA or TKA procedure), the tibial tray 102, platform 500, the platform 502, and tibial insert 104 are coupled together. To do so, the platform 500 may be coupled to the tibial tray 102 by inserting the base 520 into the track 134 of the tibial tray 102 in the manner described above in regard to FIGS. 5-10. In a similar manner, the platform 502 may be coupled to the platform 500 by positioning the platform 502 such that the stem 506 of the platform 500 is received by the track 526 of the platform 502. The tibial insert 104 may be coupled to the platform 502 by inserting the stem 530 of the tibial insert 104 into the aperture 529 of the platform 502. Once so coupled, the platform 500 is movable relative to the tibial tray 102 (e.g., in a generally anterior-posterior direction), the platform 502 is movable relative to the platform 504 (e.g., in a generally medial-lateral direction), and the tibial insert 104 is movable relative to the platform 504 (e.g., rotational direction).

During patient use, the platform 500 moves along the track 134 of the tibial tray 102 in a generally anterior-posterior direction. Similarly, the platform 502 moves along the flange 506 of the platform 500 in a generally medial-lateral direction. Additionally, because the aperture 528 and the stem 530 are substantially cylindrical in shape, the tibial insert 104 may also rotate about an axis defined by the stem 530.

It should be appreciated that the directions and/or types of movements (e.g. translational or rotational) of each component of the various embodiments of the tibial assembly 10 described above are only illustrative. In other embodiments, each movement interface (e.g., platform-to-tray, platform-to-platform, insert-to-platform) may be configured to move in any direction and/or type of movement. However, in one particular embodiment, each movement interface is restricted to a single direction and/or type of movement. For example, the platform-to-tray movement interface may be restricted to a generally anterior-posterior direction, a generally medial-lateral direction, a rotational movement, or the like. Similarly, the insert-to-platform movement interface may be restricted to a generally anterior-posterior direction, a generally medial-lateral direction, a rotational movement, or the like that is different than the movement of the platform-to-tray movement interface.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A mobile tibial assembly comprising:
   a tibial tray configured to be coupled to a surgically-prepared surface of the proximal end of a tibia;
   a unicompartmental tibial insert having an upper bearing surface configured to contact a femoral condyle and a bottom surface, the bottom surface having a first track defined therein extending in a generally medial-lateral direction; and
   a platform separate from the tibial tray and the unicompartmental tibial insert, the platform is configured to be coupled to the tibial tray and the unicompartmental tibial insert;
   wherein: (i) a first portion of the platform is configured to be inserted into the first track of the unicompartmental tibial insert such that the first portion of the platform is configured to freely slide along the first track of the unicompartmental tibial insert and the unicompartmental tibial insert is constrained so as to slide relative to the platform in only the generally medial-lateral direction when the unicompartmental tibial insert is coupled to the platform, (ii) the tibial tray includes an upper surface and a second track defined therein extending in a generally anterior-posterior direction, and (iii) a second portion of the platform is configured to be inserted into the second track of the tibial tray such that the second portion of the platform is configured to freely slide along the second track of the tibial tray and the platform is constrained so as to only slide relative to the tibial tray in only the generally anterior-posterior direction when the platform is coupled to the tibial tray.

2. The mobile tibial assembly of claim 1, wherein the second track comprises a bottom wall, a first side wall, a second side wall, a first lip extending from the first side wall over a portion of the bottom wall, and a second lip extending from the second side wall over a portion of the bottom wall, the first and second lips defining an opening therebetween.

3. The mobile tibial assembly of claim 1, wherein the platform includes a top surface and the first portion of the platform includes a stem extending upwardly therefrom.

4. The mobile tibial assembly of claim 3, wherein the first track of the unicompartmental tibial insert is configured to receive the stem of the platform.

5. The mobile tibial assembly of claim 4, wherein the first track of the unicompartmental tibial insert comprises a bottom wall, a first side wall, a second side wall, a first lip extending from the first side wall over a portion of the bottom wall, and a second lip extending from the second side wall over a portion of the bottom wall, the first and second lips defining an opening therebetween.

6. The mobile tibial assembly of claim 5, wherein each of the first and second lips includes a bottom wall oblique to the bottom wall of the first track of the unicompartmental tibial insert.

7. The mobile tibial assembly of claim 6, wherein the stem includes a flange, the flange having:
   (i) a bottom surface configured to contact the bottom wall of the first track of the unicompartmental tibial insert when the stem is received thereby, and
   (ii) a top surface oblique to the bottom surface of the flange and configured to contact the bottom surface of at least one of the first lip and the second lip of the first track of the unicompartmental tibial insert when the stem is received thereby.

8. The mobile tibial assembly of claim 5, wherein each of the first and second lips includes a bottom wall substantially parallel to the bottom wall of the track.

9. The mobile tibial assembly of claim 8, wherein the stem includes a flange, the flange having:
   (i) a bottom surface configured to contact the bottom wall of the track of the unicompartmental tibial insert when the stem is received thereby, and
   (ii) a top surface substantially parallel to the bottom surface of the flange and configured to contact the bottom surface of at least one of the first lip and the second lip of the track of the unicompartmental tibial insert when the stem is received thereby.

10. The mobile tibial assembly of claim 3, wherein the stem includes a flange, the flange having a rectangular bottom profile when viewed in plan view and being configured to restrict the movement of the unicompartmental tibial insert with respect to the platform only to the generally medial-lateral direction when the stem is received by the first track of the unicompartmental tibial insert.

11. A mobile tibial assembly comprising:
- a tibial tray configured to be coupled to a surgically-prepared surface of the proximal end of a tibia, the tibial tray including an upper surface and a first track defined therein extending parallel to the upper surface of the tibial tray along a first axis;
- a unicompartmental tibial insert having an upper bearing surface configured to contact a femoral condyle and a bottom surface, the bottom surface having a second track defined therein extending along a second axis; and
- a platform separate from the tibial tray and the unicompartmental tibial insert, wherein (i) a first portion of the platform is inserted into the first track of the tibial tray such that the first portion of the platform is configured to freely slide along the first track of the tibial tray and the platform is constrained so as to slide relative to the tibial tray along only the first axis when the platform is coupled to the tibial tray, (ii) a second portion of the platform is inserted into the second track of the unicompartmental tibial insert such that the second portion of the platform is configured to freely slide along the second track of the unicompartmental tibial insert and the unicompartmental tibial insert is constrained so as to side relative to the platform along only the second axis when the unicompartmental tibial insert is coupled to the platform, and (iii) the first axis extends transverse to the second axis.

12. The mobile tibial assembly of claim 11, wherein the platform includes a top surface and the second portion of the platform includes a stem extending upwardly therefrom.

13. The mobile tibial assembly of claim 12, wherein the second track of the unicompartmental tibial insert is configured to receive the stem of the platform.

* * * * *